(12) United States Patent
Woolfson et al.

(10) Patent No.: US 8,962,010 B2
(45) Date of Patent: Feb. 24, 2015

(54) INTRAVAGINAL DRUG DELIVERY DEVICES FOR THE DELIVERY OF MACROMOLECULES AND WATER-SOLUBLE DRUGS

(75) Inventors: David Aaron Woolfson, Belfast (IE); Karl Malcolm, Belfast (IE)

(73) Assignee: Warner Chilcott Company, LLC, Rockaway, NJ (US)

( * ) Notice: Subject to any disclaimer, the term of this patent is extended or adjusted under 35 U.S.C. 154(b) by 481 days.

(21) Appl. No.: 12/147,310

(22) Filed: Jun. 26, 2008

(65) Prior Publication Data
US 2009/0004246 A1    Jan. 1, 2009

Related U.S. Application Data

(60) Provisional application No. 60/946,299, filed on Jun. 26, 2007.

(51) Int. Cl.
| | | |
|---|---|---|
| *A61F 6/06* | (2006.01) | |
| *A61K 9/00* | (2006.01) | |
| *A61K 31/00* | (2006.01) | |
| *A61K 39/21* | (2006.01) | |
| *C07K 14/005* | (2006.01) | |
| *C07K 16/10* | (2006.01) | |
| *A61K 39/00* | (2006.01) | |

(52) U.S. Cl.
CPC .............. *A61K 9/0036* (2013.01); *A61K 31/00* (2013.01); *A61K 39/21* (2013.01); *C07K 14/005* (2013.01); *C07K 16/1063* (2013.01); *A61K 2039/541* (2013.01); *C12N 2740/16034* (2013.01); *C12N 2740/16122* (2013.01)
USPC .......................................... 424/430; 424/433

(58) Field of Classification Search
None
See application file for complete search history.

(56) References Cited

U.S. PATENT DOCUMENTS

| 2,962,023 | A | 11/1960 | Chappaz et al. |
| 3,993,072 | A | 11/1976 | Zaffaroni |
| 5,855,906 | A | 1/1999 | McClay |
| 5,972,372 | A | 10/1999 | Saleh et al. |
| 6,126,958 | A | 10/2000 | Saleh et al. |
| 6,264,973 | B1 | 7/2001 | Mahashabde et al. |
| 6,436,428 | B1 | 8/2002 | Mahashabde et al. |
| 2007/0043332 | A1 * | 2/2007 | Malcolm et al. ............. 604/500 |

FOREIGN PATENT DOCUMENTS

| WO | 9804220 A1 | 2/1998 |
| WO | 0113780 A2 | 3/2001 |
| WO | 0170154 A1 | 9/2001 |
| WO | WO 2005004837 A1 * | 1/2005 |

OTHER PUBLICATIONS

"Leuprolide", PolyPeptide Group, available at http://www.polypeptide.com/generic-peptides/leuprolide.htm (last visited Jan. 20, 2011).*
"Leuprolide", Merck Index (2000).*
M. Kajihara et al., "Development of New Drug Delivery System for Protein Drugs Using Silicone (I)", J. Controlled Release, vol. 66, pp. 49-61 (2000).
M. Kajihara et al., "Development of a New Drug Delivery System for Protein Drugs Using Silicone (II)", J. Controlled Release, vol. 73, pp. 279-291 (2001).
J. M. Kemp et al., "Continuous Antigen Delivery from Controlled Release Implants Induces Significant and Anamnestic Immune Responses", Vaccine, vol. 20, pp. 1089-1098 (2002).
S.A. Lofthouse et al., "Injectable Silicone Implants as Vaccine, Delivery Vehicles", Vaccine, vol. 20, pp. 1725-1732 (2002).
M. Maeda et al., "New Drug Delivery System for Water-Soluble Drugs Using Silicone and its Usefulness for Local Treatment: Application of GCV-Silicone to GCV/HSV-tk Gene Therapy for Brain Tumor", J. Controlled Release, vol. 84, pp. 15-25 (2002).
H. Maeda et al., "Design of Controlled-Release Formulation for Ivermectin Using Silicone", Int'l J. Pharmaceutics, vol. 261, pp. 9-19 (2003).
M. Kajihara et al., "Novel Drug Delivery Device Using Silicone: Controlled Release of Insoluble Drugs or Two Kinds of Water-Soluble Drugs", Chem. Pharm. Bull., vol. 51(1), pp. 15-19 (2003).
H. Maeda et al., "Investigation of the Release Behavior of a Covered-Rod-Type Formulation Using Silicone", J. Controlled Release, vol. 90, pp. 59-70 (2003).
F.J.M.E. Roumen et al., "Clinical Acceptability of an Ethylene-Vinyl-Acetate Nonmedicated Vaginal Ring", Contraception, vol. 59, pp. 59-62 (1999).
R. Belsky, "Water-Soluble Condom and Vaginal Contraceptive Film Insert", Vaginal Contraception: New Developments, Harper and Row, Hagerstown, Chapter 20, pp. 201-212 (1979).
J. Vartiainen et al., "Effects and Acceptability of a New 17Beta-Oestradiol-Releasing Vaginal Ring in the Treatment of Postmenopausal Complaints", Maturitas, vol. 17, pp. 129-137 (1993).

* cited by examiner

*Primary Examiner* — H. Sarah Park
(74) *Attorney, Agent, or Firm* — Fitzpatrick, Cella, Harper & Scinto

(57) ABSTRACT

An intravaginal drug delivery device comprises a device body comprising a hydrophobic carrier material having at least one channel defining at least one opening to the exterior of said device body, said at least one channel being adapted to receive at least one drug-containing insert; at least one drug-containing insert positioned in said at least one channel, said drug-containing insert capable of releasing a pharmaceutically effective amount of at least one drug suitable for intravaginal administration and containing about 1% to about 70% of at least one water-soluble release enhancer, both the drug and the water-soluble release enhancer dispersed in an insert carrier material; wherein said hydrophobic carrier material and said insert carrier material may be the same or different; and wherein said at least one drug-containing insert is exposed on said exterior of said device body when said intravaginal drug delivery device is in use.

29 Claims, 4 Drawing Sheets

SEQUENCE LISTING

```
<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: homologous to HIV-1
<220> FEATURE:
<221> NAME/KEY: DOMAIN
<222> LOCATION: (4)..(12)
<223> OTHER INFORMATION: highly conserved sequence located on gp41 of
      HIV-1
```

-continued

```
<400> SEQUENCE: 1

Gly Gly Gly Leu Glu Leu Asp Lys Trp Ala Ser Leu
1               5                   10
```

INTRAVAGINAL DRUG DELIVERY DEVICES FOR THE DELIVERY OF MACROMOLECULES AND WATER-SOLUBLE DRUGS

This application claims the benefit of U.S. Provisional Patent Application No. 60/946,299, filed Jun. 26, 2007, the entire disclosure of which is incorporated by reference herein.

BACKGROUND OF THE INVENTION

This invention relates to intravaginal drug delivery devices useful in the administration of pharmaceutically active water-soluble drugs or macromolecular agents to a female of the human or animal species.

RELATED BACKGROUND ART

Ring-shaped devices for controlled administration of drug substances into the vagina are known in the art. Several such products are already marketed, such as Estring®, Femring®, and Nuvaring®, each of which provide controlled and sustained release of steroid molecules (substantially water-insoluble drugs) over several days.

One such type of vaginal ring is the reservoir ring, which comprises a core of a polymeric material loaded with the drug substance, which is completely surrounded by a non-medicated sheath. Accordingly, the release of drug substances from such rings is dependent upon permeation (i.e., molecular dissolution and subsequent diffusion) of the core-loaded drug substance through the outer sheath. To date, the polymeric materials used in the construction of commercial vaginal rings have been limited to hydrophobic silicone elastomer and poly(ethylene-co-vinyl acetate) (PEVA) materials.

The vaginal rings described above have been found particularly useful for the release of steroids, whose relatively small molecular size and substantially water-insoluble nature permit effective permeation through the hydrophobic polymeric materials previously described, such that therapeutic concentrations may be readily achieved in the body.

Problems arise in relation to relatively water-soluble drugs that may not possess sufficient solubility in the polymer sheath of the intravaginal drug delivery device and/or whose molecular size/volume/weight are too large for rapid diffusion to permit sufficient drug delivery to the device's surface and subsequent release. Hence, one disadvantage of reservoir vaginal rings constructed from the hydrophobic polymeric materials previously described is that they do not permit permeation, and thus sustained release in therapeutic concentrations, of macromolecules and water-soluble drugs.

In an attempt to solve this problem of sustained release of therapeutic concentrations for water-soluble drugs or macromolecular agents, two vaginal ring strategies have been proposed. The first strategy involves loading the drug substance for release into a matrix ring at very high loadings (>20% w/w). In a matrix ring, the drug substance is distributed throughout the device. The combination of high loading and the availability of the drug substance on the surface of the ring device afford relatively high release rates, at least during the initial period after application. However, there are also a number of disadvantages associated with this approach. First, it is often cost prohibitive to incorporate potent and expensive therapeutic macromolecules or water-soluble drugs into matrix rings at such high loadings. Second, since release takes place from the surface of the device, a significant proportion of the drug substance within the bulk of the matrix ring is never released, instead being retained within the bulk of the ring itself.

The second strategy involves incorporation of water-soluble release enhancers into matrix rings such that water/fluid uptake into the ring promotes the release of the incorporated water-soluble or macromolecular agents. However, high loadings (typically, greater than 15% based on total device weight) of the water-soluble release enhancers are required to significantly enhance the release rate of the drug substance. Moreover, the subsequent water/fluid uptake by the water-soluble release enhancer within the device invariably leads to excessive swelling and expansion of the device such that its original shape and size are no longer maintained. Such swelling and expansion would place excessive pressure on the vaginal walls, making the device unsuitable for use.

Sustained release of water-soluble or macromolecular agents has been obtained from subcutaneously implantable devices, wherein the water-soluble drug or macromolecule and a water-soluble release enhancer are incorporated into a silicone elastomer core which is partially encapsulated with a polymeric sheath, such that the ends of the core containing the drug substance and the release enhancer are exposed to the external environment. See, e.g., M. Kajihara et al., J. Cont. Rel. 66 (2000) 49-61; M. Kajihara et al., J. Cont. Rel. 73 (2001) 279-291; J. M. Kemp et al., Vaccine 20 (2002) 1089-1098; S. A. Lofthouse et al., Vaccine 20 (2002) 1725-1732; M. Maeda et al., J. Cont. Rel. 84 (2002) 15-25; H. Maeda et al., Int'l. J. Pharm. 261 (2003) 9-19; M. Kajihara et al., Chem. Pharm. Bull. 51 (2003) 15-19; H. Maeda et al., J. Cont. Rel. 90 (2003) 59-70. In this way, release of the drug substance is achieved through uptake of the surrounding release medium/bodily fluid into the core, dissolution and removal of the water-soluble release enhancer, and concomitant dissolution and release of the drug substance. From the perspective of vaginal administration of drug substances, one disadvantage with this device, which has been specifically developed with tissue implantation in mind, is that it is not likely to be retained within the vagina owing to its size and shape of construction.

U.S. Pat. No. 6,436,428 discloses a further modified "insert" ring design, in which there is a bore extending into the ring from the ring surface, and there is an insert comprising oxybutynin and an excipient, the insert being located in the bore. The '428 patent suggests that each free end of the bore is subsequently capped, and the sealing of both ends of the bore is exemplified in Examples 3, 4, 6 and 8. Corresponding International Patent Publication No. WO 01/70154 discloses a modified "insert" ring design in which there is an open bore extending from the surface into the ring and an oxybutynin-loaded insert is then inserted into the open bore, following which the end of the open bore is then sealed with a cap. Thus, in this modified "insert" ring design, the core is, in use, completely sealed by an outer sheath that controls the oxybutynin release rate. It is believed that the caps are required to ensure that the insert is completely encapsulated within the device and surrounded by a non-medicated sheath. Such a design is usually necessary to produce zero-order release (constant daily release), or near zero-order release, via a permeation-controlled mechanism (molecular dissolution and subsequent diffusion). The absence of caps would be expected to lead to the end(s) of the core being revealed to the external environment, and thus a steadily decreasing daily release rate ($t^{0.5}$ release kinetics) would ensue. This is inappropriate for many drug therapies.

U.S. Pat. Nos. 5,972,372 and 6,126,958 disclose intravaginal rings with insertable drug-containing inserts, the object of the invention being to substantially avoid initial release bursts of steroids. In the examples, inserts placed within the rings no more than 24 hours before carrying out release rate measurements showed substantially no initial burst of steroid release.

None of the prior art discloses or suggests using a water-soluble release enhancer to facilitate sustained release of water-soluble or macromolecular drugs from an intravaginal drug delivery device comprising at least one drug-containing insert in at least one device body. Hence, there remains a need for new intravaginal drug delivery devices which allow sustained release of relatively water-soluble or macromolecular drugs from the device at pharmaceutically effective amounts.

SUMMARY OF THE INVENTION

The present invention is directed to an intravaginal drug delivery device comprising (a) a device body comprising a hydrophobic carrier material having at least one channel defining at least one opening to an exterior of said device body, said at least one channel being adapted to receive at least one drug-containing insert; and (b) at least one drug-containing insert positioned in said at least one channel, said drug-containing insert being capable of releasing a pharmaceutically effective amount of at least one drug suitable for intravaginal administration and containing at least one water-soluble release enhancer in an amount ranging from about 1% to about 70% by weight of said at least one drug-containing insert, said at least one drug and said at least one water-soluble release enhancer being dispersed in an insert carrier material; wherein said hydrophobic and insert carrier materials may be the same or different; and wherein said at least one drug-containing insert is exposed on said exterior of said device body when said intravaginal drug delivery device is in use.

In preferred embodiments of the invention, the intravaginal drug delivery device comprises first and second (or first, second and third) channels and first and second (or first, second and third) drug-containing inserts positioned in said first and second (or first, second and third) channels, respectively, wherein said first and second (or first, second and third) drug-containing inserts comprise drugs that may be the same or different.

In certain embodiments, each of the hydrophobic and insert carrier materials is a polymeric material selected from a polydimethylsiloxane, a copolymer of dimethylsiloxane and methylvinylsiloxane, a polyurethane, and a poly(ethylene-co-vinyl acetate). In further certain embodiments, each of the hydrophobic and insert carrier materials is a polymeric material selected from a polydimethylsiloxane, and a copolymer of dimethylsiloxane.

In still further preferred embodiments, the water-soluble release enhancer is selected from the group consisting of sugars or their water-soluble salts, sugar alcohols, salts, glycols, water-soluble or water-swellable polysaccharides, organic acids, amino acids, proteins, nonionic surface active agents, bile salts, organic solvents, polyethylene glycols, fatty acid esters, hydrophilic polymers, and combinations thereof.

In certain preferred embodiments, the at least one drug in the at least one insert is a water-soluble drug and/or is a macromolecular drug selected from proteins (such as peptides and polypeptides acting as antibodies, antigens, hormones or enzymes), RNA- or DNA-based molecules, vaccines, and combinations thereof.

In other optional embodiments, the device body further comprises a device body drug, or a combination of drugs, that is not considered water-soluble or macromolecular. Such a device body drug may be selected from the group consisting of contraceptives, pain and migraine agents, drugs for hormone replacement therapy, anxiety and depression agents, drugs for the treatment of premenstrual syndrome, drugs for the treatment of genito-urinary disorders, drugs for cervical ripening/induction of labor, antibacterials, antifungals, antimalarial agents, antiprotozoal agents, antiviral and antiretroviral agents, drugs for the treatment of endometriosis, antiemetic drugs and osteoporosis drugs.

The present invention is further directed to a method of preparing the intravaginal drug delivery device of the first embodiment of the invention comprising the steps of (a) molding said hydrophobic carrier material in the form of said device body defining at least one channel; and (b) inserting said at least one drug-containing insert into said at least one channel such that said drug-containing insert is exposed on said exterior of said device body. In a preferred embodiment, the method further comprises the step of curing the device body.

The present invention is still further directed to a method of intravaginally administering a drug to a female comprising the step of inserting the intravaginal drug delivery device of the first embodiment into the vagina.

DETAILED DESCRIPTION OF THE INVENTION

Figure 1:
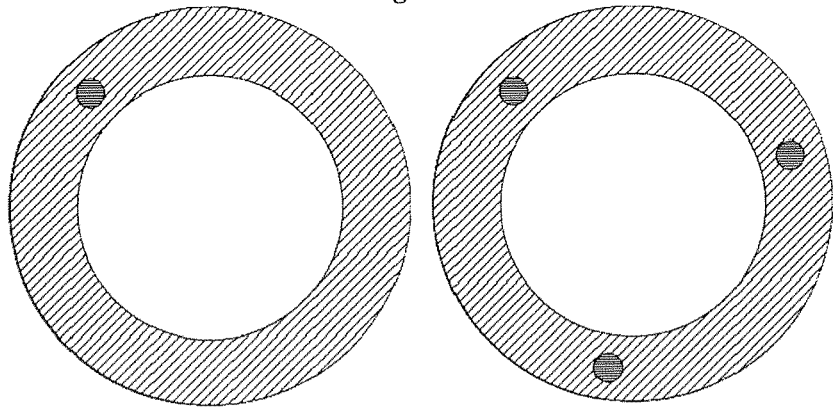
FIG. 1 shows, schematically, vaginal rings according to this invention, containing either one or three inserts.

The present invention relates to intravaginal drug delivery devices useful in the administration of drugs that are water-soluble and/or macromolecular, which have heretofore been difficult to formulate for sustained release from an intravaginal drug delivery device. By virtue of the inventive intravaginal drug delivery device configuration, sustained intravaginal release of the water-soluble and/or macromolecular agents can be achieved in order to treat or prevent disease.

As used herein, "pharmaceutically active agent", "agent", "drug", "device body drug", "active agent", "active ingredient", etc., are used interchangeably and refer to any agent (or prodrug thereof) capable of defending against, or treating, a disease or cosmetic state in the human or animal body. Such pharmaceutically active agents are usually organic but may be inorganic, may be hydrophilic or lipophilic, may be prophylactically, therapeutically and/or cosmetically active, systemically or locally. As used herein, "prophylactically active" refers to an agent's effectiveness in defending against a disease state in the human or animal body, preferably the human body. As used herein, "therapeutically active" or "pharmaceutically effective" refers to an agent's effectiveness in treating a disease state in the human or animal body, preferably the human body. As used herein, "cosmetically active" refers to an agent's effectiveness in defending against or treating a cosmetic condition in or on the human or animal body, preferably the human body. Such agents are intended to be released into vaginal fluid by diffusion out of the intravaginal drug delivery device and may exert their effect either locally or systemically.

As used herein, "release enhancer" refers to any material, when used in combination with a drug, capable of increasing cumulative release of the drug for a given time period when compared with the cumulative release of the drug in the absence of the release enhancer. A "water-soluble release enhancer" as used herein is any release enhancer (as defined above) having water solubility at any pH at 37° C. of greater than about 1% w/v, more preferably greater than about 5% w/v and most preferably greater than about 20% w/v. As used herein, "water-soluble drug" refers to any drug having water solubility at 37° C. of greater than about 5% w/v, more preferably greater than about 10% w/v and most preferably greater than about 20% w/v. As used herein, "macromolecular" refers to molecules having a molecular weight of more than 400 Daltons, more preferably more than 1000 Daltons, and most preferably more than 2500 Daltons. As used herein, "sustained release" refers to the ability to release a drug substance over relatively long periods of time, for example, multiple days or weeks, including 1-7 days, 1-14 days or 1-28 days, or longer, thereby reducing the dosing frequency. As used herein, "pharmaceutically effective amount" refers to an amount of drug required to bring about a desired prophylactic, therapeutic or cosmetic result.

The first embodiment of the present invention is directed to an intravaginal drug delivery device comprising: (a) a device body comprising a hydrophobic carrier material having at least one channel defining at least one opening to an exterior of said device body, said at least one channel being adapted to receive at least one drug-containing insert; and (b) at least one drug-containing insert positioned in said at least one hollow internal channel, said drug-containing insert being capable of releasing a pharmaceutically effective amount of at least one drug suitable for intravaginal administration and containing at least one water-soluble release enhancer in an amount ranging from about 1% to about 70% by weight of said at least one drug-containing insert, said at least one drug and said at least one water-soluble release enhancer being dispersed in an insert carrier material. The hydrophobic and insert carrier materials may be the same or different, and the at least one drug-containing insert is exposed on the exterior of the device body when the intravaginal drug delivery device is in use.

Importantly, the device body of the first embodiment has at least one channel defining at least one opening to an exterior of the device body. Each channel is open on one, and may be open on both, end(s). While channels are typically formed in a device body so as to be substantially perpendicular to the main plane of the device body, channels may be formed with any orientation with respect to the device body. Similarly, while the internal shape of a channel is typically columnar or cylindrical, channels may be formed in any shape capable of receiving at least one like-shaped or compatibly-shaped drug-containing insert(s); another example of the shape a channel may take includes a cone. The opening at one, or both, end(s) need not be circular and, for example, may be oval in shape. In certain preferred embodiments, the device body has one, two or three or even up to ten, channels in which to receive one or more drug-containing inserts, and the present invention expressly includes intravaginal drug delivery devices with more than three such channels. Exemplary devices with one and three channels are shown in FIG. 1. When more than one channel is present, each channel may have the same or different orientation with respect to the main plane of the device body, the same or different overall shape and the same or different overall dimensions.

Additionally, each channel may receive at least one drug-containing insert. When more than one channel is present, the at least one drug-containing insert contained in one channel may comprise the same or different drug than the at least one drug-containing insert contained in another channel. Likewise, when more than one drug-containing insert is received by a given channel, the drug in those inserts may be the same or different.

The intravaginal drug delivery device of the first embodiment of the present invention also comprises at least one drug-containing insert. The at least one insert is positioned in the at least one channel of the device body in such a manner as to expose at least one end of the insert via the opening(s) at the exterior of the device body. Each insert comprises a water-soluble release enhancer and is capable of releasing a pharmaceutically effective amount of at least one drug suitable for vaginal administration.

The drug is present in the insert in an amount effective to release a pharmaceutically effective amount (defined above), preferably in an amount ranging from about 0.001% to about 50% w/w, more preferably ranging from about 0.05% to about 30% w/w of the insert and most preferably ranging from about 0.5% w/w to about 25% w/w of the insert.

Drugs suitable for intravaginal administration which can be employed in the at least one drug-containing insert for use in the present invention are those considered water-soluble (defined above) and/or or macromolecular (defined above). Typical drugs in those categories are intended for the vaginal protection against HIV and other vaginal infections and might include vaginal antibodies or alternative microbicidal drugs. Typical drugs in those categories include, without limitation, proteins (such as peptides and polypeptides acting as antibodies, antigens, hormones or enzymes), RNA- or DNA-based molecules, vaccines, and combinations thereof.

Exemplary proteins (such as peptides and polypeptides) include, without limitation, antibodies, antigens, adrenocorticotropic hormone, angiotensin, beta-endorphin, blood factors, bombesin, calcitonin, calcitonin gene relating polypeptide, cholecystokinin-8, colony stimulating factors, desmopressin, endothelin, enkephalin, erythropoietins, gastrins, glucagon, human atrial natriuretic polypeptide, interferons, insulin, growth factors, growth hormones, interleukins, luteinizing hormone release hormone, monoclonal antibodies, melanocyte stimulating hormone, muramyldipeptide, neurotensin, oxytocin, parathyroid hormone, peptide T, secretin, somatomedins, somatostatin, thyroid stimulating hormone, thyrotropin releasing hormone, thyrotropin stimulating hormone, vasoactive intestinal polypeptide, vasopressin, and their analogues or derivatives. Exemplary monoclonal antibodies include, without limitation, HIV monoclonal antibody 2F5, rituxumab, infliximab, trastuzumab, adalimumab, omalizumab, tositumomab, efalizumab, and cetuximab. Exemplary antigens include, without limitation, vaccine candidates such as gp 140. Exemplary erythropoietins include, without limitation, epoetin alpha, darbepoetin alpha, and epoetin beta. Exemplary interferons include, without limitation, interferon alpha-2b, peg interferon alpha-2b, interferon alpha-2b+ribavirin, interferon alpha-2a, pegylated interferon alpha-2a, interferon beta-1a, and interferon beta. Exemplary insulins include, without limitation, regular insulin, insulin lispro, insulin aspart, insulin glulisine, isophane insulin, insulin glargine, insulin detemir, and mixed insulins. Exemplary blood factors include, without limitation, alteplase/tenecteplase and rhesus factor VIIa. Exemplary colony stimulating factors include, without limitation, filgrastim and pegfilgrastim. Exemplary growth hormones include, without limitation, sumatropin and r-sumatropin. Exemplary interleukins include, without limitation, interleukin-2. Exemplary growth factors include, without limitation, platelet derived growth factor and basic fibroplast growth factor.

Exemplary RNA- or DNA-based molecules include, without limitation, oligonucleotides, aptamers, ribozymes, DNAzymes and small interfering RNAs, for either vaccination against sexually transmitted infections or microbicidal activity against sexually transmitted microorganisms; examples of such infections and associated microorganisms include, but are not limited to, human immunodeficiency virus (HIV) infection, herpes simplex virus (HSV) infection and human papilloma virus (HPV) infection.

Exemplary vaccines include, without limitation, whole viral particles, recombinant proteins, subunit proteins such as gp41, gp120 and gp140, DNA vaccines, plasmids, bacterial vaccines, polysaccharides such as extracellular capsular polysaccharides, and other vaccine vectors The at least one drug-containing insert also comprises at least one water-soluble release enhancer in an amount ranging from about 1% to about 70%, more preferably from about 1% to about 60%, and most preferably from about 1% to about 55% by weight of the insert. When the drug is macromolecular, the at least one drug-containing insert comprises at least one water-soluble release enhancer in an amount ranging from about 1% to about 70%, more preferably from about 1% to about 60%, and most preferably from about 5% to about 55% by weight of the insert. Alternatively, when the drug is water-soluble, the at least one drug-containing insert comprises at least one water-soluble release enhancer in an amount ranging from about 15% to about 70%, more preferably from about 15% to about 60%, and most preferably from about 15% to about 55% by weight of the insert. Further alternatively, when the drug is water-soluble and macromolecular, the at least one drug-containing insert comprises at least one water-soluble release enhancer in an amount ranging from about 15% to about 70%, more preferably from about 15% to about 60%, and most preferably from about 15% to about 55% by weight of the insert.

Examples of water-soluble release enhancers include, without limitation, sugars such as monosaccharides or disaccharides, including glucose or lactose, or their water-soluble salts; sugar alcohols such as mannitol; salts such as sodium chloride, sodium glutamate or sodium citrate; glycols; water-soluble or water-swellable polysaccharides, preferably cellulose derivatives such as croscarmellose (cross-linked carboxymethylcellulose) or hydroxyethylcellulose; organic acids such as ascorbic acid; amino acids such as glycine; proteins such as gelatins or albumins; nonionic surface active agents; bile salts; organic solvents, such as ethoxydiglycol; polyethylene glycols; fatty acid esters, preferably containing 2 to 20 carbon atoms, of which myristate esters are preferred; hydrophilic polymers such as polyvinyl pyrrolidone (PVP) or polyethylene glycol (PEG), and combinations thereof. Examples of preferred water-soluble release enhancers include, without limitation, sugars such as monosaccharides or disaccharides, including glucose or lactose, or their water-soluble salts; water-soluble or water-swellable polysaccharides, preferably cellulose derivatives such as croscarmellose (cross-linked carboxymethylcellulose) or hydroxyethylcellulose; amino acids such as glycine; proteins such as gelatins or albumins; hydrophilic polymers such as polyvinyl pyrrolidone (PVP) or polyethylene glycol (PEG), and combinations thereof. Glycine is a preferred water-soluble release enhancer. Albumins are preferred release enhancers for protein-based drugs as they would serve to protect (via a competitive mechanism) the drug from various degradation processes. Release of a macromolecular or water-soluble agent occurs predominantly from the open end(s) of the channels, at which point the end(s) of the drug-containing insert is/are exposed.

One purpose of the water-soluble release enhancer contained within the insert is to absorb aqueous fluid (including water itself) and thus enhance the release of the therapeutic agent. Without being bound by theory, it is thought that the water-soluble release enhancer attracts aqueous fluid under an osmotic gradient. In use, the intravaginal drug delivery device of the invention is inserted into the vagina. The volume defined by the vaginal walls is the vaginal environment and contains the vaginal fluid which includes water. In use, the vaginal fluid contacts the exposed surface of the insert and the vaginal fluid dissolves the water-soluble release enhancer of the insert, causing pores to form in the insert. The increased porosity of the insert brings a greater surface area of the insert into contact with the vaginal fluid (specifically, e.g., the water of the vaginal fluid), thereby allowing the macromolecules and the water-soluble drugs to dissolve in the vaginal fluid of the vaginal environment.

In a preferred embodiment of the invention, the at least one water-soluble release enhancer achieves cumulative release over days 1 to 7 under sink conditions at 37° C. from a drug delivery device of the present invention comprising a single insert having a diameter of 3.0 mm that is at least about 5% higher than cumulative release from a drug delivery device comprising a device body and a single insert having a diameter of 3.0 mm containing less than about 1% of at least one water-soluble release enhancer. In further preferred embodiments, the at least one water-soluble release enhancer achieves cumulative release over days 1 to 7 under sink conditions at 37° C. from a drug delivery device of the present invention that is at least about 10% higher, at least about 20% higher, at least about 25% higher, at least about 50% higher, at least about 75% higher, or at least about 100% higher than cumulative release from a drug delivery device comprising a device body and a single insert having a diameter of 3.0 mm containing less than about 1% of at least one water-soluble release enhancer.

The insert carrier material contains both the drug and the water-soluble release enhancer. In other words, the at least one drug and the at least one water-soluble release enhancer are dispersed in an insert carrier material. The insert carrier material may be the same as or different from the hydrophobic carrier material of the device body (discussed below); materials suitable for use as the insert carrier material are discussed below with regard to the hydrophobic carrier material of the device body. For example, the insert carrier material may be a silicone elastomer such as a silicone, such as a 40:1 mixture of silicone elastomer base MED-6382 and a suitable crosslinking agent such as tetrapropyl orthosilicate, to which a catalyst such as stannous octoate catalyst (0.5%, w/w) was added.

Without being bound by theory, it is thought that hydrophilic insert carrier materials, such as hydrogels, polyethylene glycol plugs, etc., would not provide sustained release, i.e., prolonged release over multiple days/weeks. Such hydrophilic carrier materials generally release drugs at much faster rates, since water can be taken up by them much more quickly. Hydrophobic insert carrier materials are preferred. In the inserts used in the present invention, the release rate is controlled through the ratio of the hydrophobic insert carrier material to the water-soluble release enhancer, as will be readily appreciated by one of ordinary skill in this art. It is this feature that permits sustained release profiles to be achieved.

The at least one drug-containing insert may optionally comprise at least one pharmaceutically acceptable non-water-soluble release enhancer in an amount ranging from about 1% to about 25%, more preferably from about 5% to about 15%, and most preferably from about 10% by weight of the insert. As used herein, "non-water-soluble release enhancer" refers to any release enhancer having water solubility at any pH at 37° C. of less than about 1% w/v. One suitable non-water-soluble release enhancer is silicone oil in an amount ranging from about 1% to about 25%, more preferably from about 5% to about 15%, and most preferably from about 10% by weight of the insert.

The at least one drug-containing insert may optionally comprise a pharmaceutically acceptable filler to enhance the mechanical strength of the insert. The filler may be the same or different from a filler employed in the device body (discussed below). The amount of filler used in the insert will depend on the desired properties of the insert but, typically, ranges from about 5 to about 35 parts, more preferably from about 7.5 to about 27.5 parts, by weight per 100 parts by weight of the insert.

Preferably, an insert has a cross-sectional diameter (if circular in transverse cross-section) ranging from about 0.5 mm to about 8 mm, more preferably from about 1 mm to about 5 mm, and most preferably from about 2 mm to about 4 mm; additionally the insert preferably has a length ranging from about 2 mm to about 30 mm, optionally from about 2 mm to about 20 mm, further optionally from about 5 to about 15 mm.

In preferred embodiments, the diameter of the insert (if circular in transverse cross-section) relative to the channel may vary slightly; it may be substantially equal to or slightly greater or smaller than the channel diameter. In optional embodiments, the insert diameter is substantially equal to or even slightly greater than that of the channel, such that following insertion or formation of the insert into the channel, surface contact is maintained between the outer longitudinal surfaces of the insert and the surface of the channel. In a certain optional embodiment, the dimensions of the insert exceed the dimensions of the channel by about 1 mm in all directions. Ultimately the dimensions of the insert are determined by such factors as the amount of drug to be delivered to the subject, the time period over which the drug is to be delivered, and the permeation characteristics of the drug.

In a preferred embodiment, the at least one drug-containing insert is a substantially cylindrical rod. More preferably, the insert defines a right circular cylinder and at least one end of the at least one drug-containing insert is partly or fully exposed, in use, to the vaginal environment. Optionally, the at least one drug-containing insert is substantially circular in transverse cross-section and extends substantially radially, inwardly or outwardly, through the device and, in this event, the insert has a length from about 2 mm to about 10 mm. While the insert preferably takes the form of a cylindrical rod, the shape can be any suitable to be received in a correspondingly-shaped channel of the device body.

It will be appreciated that most, if not all, of the drug is released from the insert by a multistep process involving (i) the influx of fluid into the insert via the free end(s) exposed, (ii) the dissolution and removal of the water-soluble release enhancer, (iii) the subsequent production of channels and pores within the bulk of the insert, and (iv) the concomitant dissolution and diffusion of the drug through the insert and out the exposed free ends, in use, to the vaginal environment. Among the important factors governing release from the intravaginal drug delivery devices of the present invention are the solubility of the insert carrier material and/or insert water-soluble release enhancer in vaginal fluid, the surface area of the insert exposed to the vaginal environment and the distance the drug must diffuse within the insert to reach this "exposed" surface area.

Inserts for use in the present invention may be prepared by any suitable method such as injection molding or extrusion. The inserts may also be formed in situ as described below. For thermolabile drugs, the inserts may be prepared at low temperatures in order to retain drug stability; for thermostable drugs, the inserts may be prepared at elevated temperatures.

The intravaginal device of the present invention is typically an intravaginal ring (IVR), though it is intended that the term "intravaginal drug delivery device" embraces all device designs such as, but not limited to, other complete or partial toroid-shaped devices, as well as ovoid and cylindrical devices. Intravaginal rings of the present invention may have any conventional design as a starting point, i.e., they may be of the matrix, shell or reservoir design. See, e.g., T. M. Jackanicz, Vaginal Contraception: New Developments. Harper and Row, Hagerstown, pp. 201-212, 1979, for a description of various intravaginal ring designs.

Regardless of design, the intravaginal drug delivery device of the first embodiment of the present invention comprises a device body that takes the form of an otherwise conventional matrix ring, reservoir ring (comprising a core and sheath), or shell ring (comprising a central member, a core and a sheath). In other words, the device body of the present invention may include any component typically of use in conventional intravaginal drug delivery devices such as IVRs. When present, a sheath, which is an outermost layer of the device body, i.e., surrounds other device body components, contains openings corresponding to the at least one channel so as to ensure exposure of the drug-containing insert to the exterior of the device body and to the use environment. When present, a drug-containing core has such a shape and position within the device body so as not to interfere with the at least one channel, i.e., there is no intersection of channel(s) with any core(s).

The device body (and any components thereof) may be fabricated from any pharmaceutically acceptable hydrophobic carrier material. However, the device body should be, in use, solid or semi-solid, i.e., capable of conforming to the shape of the space available for the device body, e.g., fabricated from a material selected from a shape-retaining material, a thermosetting material, or a thermoplastic material. For example, the device body may comprise an elastomeric or non-elastomeric, polymeric or non-polymeric hydrophobic carrier material. In any event, the device body must be biocompatible, i.e., suitable for insertion in the human or animal body.

Suitable polymeric hydrophobic carrier materials include, but are not limited to, silicones, poly(ethylene-co-vinyl acetate), styrene-butadiene-styrene block copolymers, polyvinyl chloride, polyvinyl acetate, poly(vinyl alcohol), polyesters, polyurethanes, polyacrylonitriles, polypropylene, polymethylpentene, polybutadiene, and mixtures thereof. For example, the hydrophobic carrier material may be a silicone, such as a 40:1 mixture of silicone elastomer base MED-6382 and a suitable crosslinking agent such as tetrapropyl orthosilicate, to which a catalyst such as stannous octoate catalyst (0.5%, w/w) was added. Device bodies made of such polymeric hydrophobic carrier materials provide rapid release of any small substantially water-insoluble drugs when present in the hydrophobic carrier material of the device body.

Suitable non-polymeric hydrophobic carrier materials include, but are not limited to, pharmaceutically acceptable low-melting point waxes such as stearyl alcohol or semi-synthetic glycerides of saturated fatty acids (preferably those of $C_8$ to $C_{18}$), or a mixture thereof. For example, the drug may be dispersed within a low-melting point wax and molded at low temperature into a shape compatible with the intravaginal drug delivery device design.

Elastomers are preferred polymeric hydrophobic carrier materials. Elastomers are defined as amorphous, or predominantly amorphous, high molecular weight polymers above their glass transition temperature, which can be stretched and retracted rapidly, exhibit high strength and modulus when stretched, and recover fully whenever the stress is removed. Generally, these elastomers are crosslinked to restrain gross mobility, either permanently (a covalently-crosslinked elastomer) or reversibly (a thermoplastic elastomer). Elastomers are typically chosen from the room-temperature vulcanizing type of organopolysiloxanes, for example, poly(dimethylsiloxane). Another silicone elastomer suitable for use herein is a copolymer of dimethylsiloxane and methylvinyl siloxane. Non-silicone elastomers that are known in the art include, but are not limited to, poly(ethylene-co-vinyl acetate) (Roumen et al., Contraception, 59 (1999) 59-62) and styrene-butadiene-styrene block copolymer (Vartiainen et al., Maturitas, 17 (1993) 129-137). A preferred hydrophobic carrier material is derived from hydroxyl-terminated organopolysiloxanes (such as polydimethylsiloxanes as disclosed in U.S. Pat. No. 5,855,906, the disclosure of which is incorporated by reference herein) of the RTV (room temperature vulcanizing) type, which harden to elastomers at room temperature or higher, following the addition of cross-linking agents in the presence of curing catalysts. Other silicone elastomers suitable for the hydrophobic carrier material include additiontype, two-component poly(dimethylsiloxane)s which are platinum catalyzed at room temperature or under elevated temperatures, one-component poly(dimethylsiloxane)s, and silicone elastomers functionalized with fluorine, benzyl and other moieties.

In preferred embodiments, the hydrophobic carrier material and/or the insert carrier material is a polymeric material selected from a silicone elastomer such as polydimethylsiloxane or a copolymer of dimethylsiloxane and methylvinylsiloxane, a polyurethane, or a poly(ethylene-co-vinyl acetate). A preferred hydrophobic carrier material and/or insert carrier material is commercially available as Nusil Med 7.6382 from Nusil Technology, Carpinteria, Calif., USA.

If a sheath is present, the sheath comprises a sheath carrier material. Hydrophobic sheath carrier materials are preferred. Preferred hydrophobic sheath carrier materials are silicones; more preferred are elastomers, especially if the remainder of the device body is not elastomeric. In this embodiment, the elastomeric properties of the sheath confer sufficient flexibility on the composite intravaginal drug delivery device to allow placement in, and retention within, the vagina. Most preferably, a sheath comprises a hydrophobic carrier material which is a silicone elastomer derived from hydroxyl-terminated organopolysiloxanes.

The device body may optionally contain additional ingredients such as drugs, particulate filler materials, and other excipients such as diffusion inhibitors, penetration enhancers, water-soluble release enhancers and combinations thereof.

At least one drug suitable for intravaginal release from the device body can be employed for use in the present invention. Drugs suitable for inclusion in the device body are those typically suitable for conventional formulation, i.e., drugs not considered water-soluble (as defined above) or macromolecular (as defined above). Such drugs not considered water-soluble or macromolecular, and referred to herein as device body drugs, include, without limitation, contraceptives, pain and migraine agents, drugs for hormone replacement therapy, anxiety and depression agents, drugs for the treatment of premenstrual syndrome, drugs for the treatment of genitourinary disorders, drugs for cervical ripening/induction of labor, antibacterials, antifungals, antimalarial agents, antiprotozoal agents, antiviral and antiretroviral agents, drugs for the treatment of endometriosis, anti-emetic drugs and osteoporosis drugs. Preferably a device body drug is present in the device body in a pharmaceutically effective amount. Typically, the amount of device body drug used in the device body ranges from about 0.005% to about 65% w/w, and more preferably ranging from about 0.5% to about 50% w/w of the device body. In certain embodiments of the invention, a drug may, in addition or in substitution, be present in a sheath in an amount ranging from about 0.001% to about 65% w/w of the sheath.

Exemplary contraceptives suitable for intravaginal release from the device body, the sheath or both, include, without limitation, desogestrel, dienestrol, diethylstilberol, estradiol, estriol, estradiol-3-acetate, ethinyl estradiol, etonogestrel, gestodene, levonorgestrel, medroxyprogesterone, medroxyprogesterone acetate, mestranol, norethisterone, norgestimate, nonoxynol-9, norethisterone acetate, progesterone, testosterone, testosterone acetate, ST-1435 (a progestin) and tibolone.

Exemplary drugs for hormone replacement therapy and suitable for intravaginal release from the device body, the sheath or both, include, without limitation, dehydroepiandrosterone sulphate, dienestrol, diethylstilberol, estrogens such as estradiol, estriol, estradiol-3-acetate, ethinyl estradiol, gestodene, levonorgestrel, luteinizing hormone releasing hormone, norethisterone, norethisterone acetate, progesterone, ST-1435, testosterone, and testosterone acetate.

Exemplary osteoporosis and/or hormone replacement therapy drugs and suitable for intravaginal release from the device body, the sheath or both, include, without limitation, selective estrogen receptor modulators (SERMs) such as raloxifene.

Suitable particulate filler materials may be used to enhance the mechanical strength of the device body or the sheath. Fillers suitable for use include, without limitation, finely divided, reinforcing or extending fillers such as high surface area fumed and precipitated silicas, clays such as kaolin, crushed quartz, diatomaceous earths, calcium carbonate, barium sulphate, iron oxide, titanium dioxide and carbon black. The amount of filler (when present) employed in a device body will depend on the desired properties of the finished device. Typically the amount of filler ranges from about 5 to about 35 parts, and more preferably from about 7.5 to about 27.5 parts by weight, per 100 parts by weight of the device body. The sheath can contain filler in an amount ranging from about 0 to about 35 parts by weight per 100 parts by weight of the sheath.

Suitable diffusion inhibitors may be used in the device body to reduce or prevent drug release from a reservoir via diffusion through a sheath. Such excipients are often contained in a sheath and are often the same materials used as fillers (described above); accordingly, they act so as to increase the tortuosity of the diffusional path of an active agent, i.e., increase the diffusional distance that the active agent must traverse through the device body prior to its release from said device.

Suitable chemical penetration enhancers may be used in the device body to enhance drug absorption across the vaginal epithelium; for example, surface active agents that have a reversible effect on the arrangement of epithelial lipids such as oleic acid or agents that directly affect tight junctions between epithelial cells may be used.

Suitable water-soluble release enhancers may be used in the device body for the purposes of modifying the release characteristics of a pharmaceutically active agent contained in the device body. In addition to including water-soluble release enhancers in the insert, water-soluble release enhancers may also be included in the device body. In so doing, those skilled in the art will appreciate that care must be taken not to use too high a loading, otherwise excessive swelling of the intravaginal drug delivery device would ensue. However, the use of water-soluble release enhancers in the device body will not provide for effective release of water-soluble drugs or macromolecules; rather, the release rates for those compounds that may already be effectively released from a conventional device body may be modified using the same water-soluble release enhancers as for the inserts. Suitable water-soluble release enhancers for inclusion in the device body are the same as discussed above with regard to the insert. When present in the device body, such water-soluble release enhancers are typically present in an amount of less than 10%, optionally less than 5% and further optionally less than 1% by weight of the device body.

Overall, the geometry of the intravaginal drug delivery device of the present invention may be chosen according to theoretical calculations by methods known to those skilled in the art such that the desired daily release of the at least one drug from the insert is achieved and sustained for the desired duration of, for example, 1-7 days, or 1-14 days or 1-28 days, or longer. For an intravaginal drug delivery device, the desired "geometry" would encompass, for example, the length, width and cross-sectional area of the device. For an intravaginal ring, the term "geometry" encompasses features such as the overall diameter of the ring, the cross-sectional diameter of the ring and the length of the core if present, the ratio of the core (if present) diameter to the diameter of the complete device in cross-section. A preferred geometry is a reservoir ring having an overall or outer diameter of preferably from about 45 to about 60 mm, more preferably from about 52 to about 60 mm; a core diameter of preferably from about 1 to about 7 mm, more preferably from about 2 to about 6.5 mm, most preferably from about 3 to about 6 mm; a cross-sectional diameter of from about 4 to about 10 mm, more preferably from about 4.5 to about 10 mm, most preferably from about 5.5 to about 9.5 mm; and a core length of from about 2 to about 200 mm.

A second embodiment of the present invention is directed to a method of preparing an intravaginal drug delivery device according to the first embodiment of the invention, the method comprising the steps of (a) molding the hydrophobic carrier material in the form of the device body defining at least one channel; and (b) inserting the at least one drug-containing insert into the at least one channel such that the drug-containing insert is exposed on the exterior of the device body. Optionally, the method of the second embodiment also includes the step of curing the device body. In a preferred embodiment, the hydrophobic carrier material is an elastomeric material that is molded with at least one removable rod or other suitable device to produce a continuous, annular ring body with a corresponding predetermined number of channels. In preferred embodiments, the molding step is conducted in the presence of a catalyst. The insert may be prepared by mixing the drug with the insert carrier material (optionally, an elastomeric material), followed by molding and then optionally curing. In another preferred embodiment, the insert may be cured in situ in the device body. In these embodiments, the drug-containing insert may be effectively introduced by injecting a mixture of the drug, the insert carrier material and a suitable catalyst into the hollow internal channel of the device body so that the drug-containing insert is formed in situ.

The invention is not limited to the embodiments described and exemplified herein, which may be modified and amended without departing from the scope of the present invention. Thus, for instance, it will be obvious to those skilled in the art that the technique of injection molding referred to herein may be replaced in whole or in part by other manufacturing techniques that will produce the same end product, notably the technique of extrusion.

A further embodiment of the invention is directed to an intravaginal drug delivery device made according to the method of the second embodiment of the invention.

Still another embodiment of the invention is directed to a method of intravaginally administering a drug to a female over a predetermined time period comprising the step of inserting the intravaginal drug delivery device of the first embodiment of the invention into the vagina so that the drug will be intravaginally delivered to the female for a predetermined period of time that could range from 1-7 days or 1-14 days or 1-28 days or longer, such as 1-360 days, optionally 1-90 days.

Specific embodiments of the invention will now be demonstrated by reference to the following general methods of manufacture and examples. It should be understood that these examples are disclosed solely by way of illustrating the invention and should not be taken in any way to limit the scope of the present invention.

General Method of Intravaginal Device
Manufacture—Examples 1-3

Silicone elastomer base MED-6382 and the crosslinking agent tetrapropyl orthosilicate were blended 40:1. Stannous octoate catalyst (0.5%, w/w) was added and the blend injected into specially designed vaginal ring molds. The mix was cured at 80° C. for 2 min, producing silicone elastomeric vaginal rings containing one or three channels and with the following dimensions: 7.6 mm cross-sectional diameter, 43.0 mm internal diameter, 58.0 mm external diameter and a channel insert diameter of 3.0 mm. Drug-loaded silicone rods were manufactured by mixing a desired amount of drug with the appropriate silicone elastomer in a DAC 150 FVZ-K Speedmixer for 30 seconds at 3000 rpm. The mixture was then injected into PVC tubing of 3 mm diameter and allowed to cure for 24 hours at room temperature. The PVC tubing was cut into desired lengths, and the PVC sheath carefully removed from the cured silicone elastomer rods using a scalpel.

Protocol for In Vitro Release Studies—Examples 1-3

A single drug-loaded rod was inserted into a channel within a vaginal ring. All of the in vitro daily release profiles for the intravaginal ring devices of the invention were determined under sink conditions. This mimics the in vivo situation. The term "sink conditions" refers to that set of experimental conditions in vitro that effectively simulates the active haemoperfusion that occurs in vivo, and which results in a maximum drug diffusion rate, at any given time, across the aqueous boundary layer. Thus, the solubility characteristics of the drug will determine the choice of a suitable dissolution medium.

The in vitro daily release profiles for the intravaginal ring devices of Examples 1-3 of the invention were determined under sink conditions in laboratory grade water. The drug delivery devices of the present invention were placed into suitable flasks containing 20 ml of water and placed in an orbital (60 rpm) shaking incubator at 37° C. Daily sampling with replacement of the release medium continued for several days, followed by regular sampling thereafter. Release was quantified by HPLC, and the daily and cumulative release data were collected.

It will be readily appreciated by those skilled in the art that the release rates and release amounts demonstrated in the following examples are not restrictive and can be manipulated to alter the release rate and/or release amount, as desired, by, for example, changing the loading of drug substance in the insert, changing the loading and/or type of water-soluble release enhancer in the insert, and/or changing the dimensions of the insert, or a mixture of some or all of these parameters.

EXAMPLE 1

Sustained Release of Bovine Serum Albumin from Intravaginal Drug Delivery Devices Silicone elastomer vaginal rings containing a single channel were manufactured according to the general method described above. Silicone elastomer inserts containing 1.0% w/w BSA, 20.0% w/w water-soluble release enhancer (glycine, glucose, PVP or PEG 3400) and 79.0% w/w LSR-9-9508-30 silicone elastomer (Dow Corning) were also manufactured according to the general method described above, with a desired length of 7.6 mm. A single insert was inserted into the channel formed in the silicone elastomer vaginal ring. In vitro release experiments were conducted as described above, except quantification was performed using a BCA™ [bicinchoninic acid, a compound used in the kit to assay for the protein] protein microassay kit (Pierce, US). The cumulative release data over fourteen days are presented in Table 1.

TABLE 1

Cumulative release of bovine serum albumin (BSA) from vaginal rings containing a single insert constructed from various water-soluble release enhancers. BSA loading = 1.0% w/w, water-soluble release enhancer loading of 20.0% w/w.

| Day | No Water-Soluble Release Enhancer | 20% Glycine | 20% Glucose | 20% PVP | 20% PEG |
|---|---|---|---|---|---|
| 1 | 20.7 | 67.9 | 131.0 | 29.3 | 23.0 |
| 2 | 23.0 | 86.3 | 172.4 | 38.0 | 27.9 |
| 3 | 44.7 | 107.0 | 188.8 | 43.5 | 45.3 |
| 4 | 59.5 | 118.6 | 196.9 | 83.1 | 85.0 |
| 7 | 71.7 | 142.9 | 238.1 | 92.7 | 87.4 |
| 8 | 77.6 | 158.5 | 250.3 | 98.0 | 95.9 |
| 9 | 82.0 | 174.4 | 255.6 | 103.2 | 102.0 |
| 10 | 91.2 | 184.8 | 274.9 | 112.0 | 106.0 |
| 11 | 92.9 | 202.4 | 280.6 | 116.2 | 106.0 |
| 14 | 92.9 | 219.2 | 290.5 | 117.9 | 131.6 |

It will be appreciated that BSA is not, of itself, a drug. It was chosen herein as a protein with a molecular weight of 66.43 kDa, to demonstrate sustained release over 14 days of a macromolecule.

EXAMPLE 2

Sustained Release of the Monoclonal Antibody 2F5 from Intravaginal Drug Delivery Devices Silicone elastomer vaginal rings containing a single channel were manufactured according to the general method described above. Silicone elastomer inserts containing 2F5 were prepared as follows. Water was first removed from the 2F5 stock solution (13.01 mg/ml) by freeze-drying 2F5 solution (10% w/w) mixed with glycine (10% w/w). After drying, the remaining portion of glycine (30% w/w) was mixed with the freeze-dried 2F5-glycine cake. Uncovered silicone inserts were manufactured by mixing the 2F5-glycine mix with silicone elastomer (LSR-9-9508-30, 50% w/w) (Dow Corning) in a DAC 150 FVZ-K Speedmixer for 30 seconds at 3000 rpm. The mixture was then inserted into a 2 ml syringe and manually injected into PVC tubing of 3 mm diameter and allowed to cure for 24 hours at RT. After this time, the rods were cut into 9 mm lengths, and the PVC sheath carefully removed from the cured silicone elastomer inserts using a scalpel. A single insert was then placed into the channel of a vaginal ring device. In vitro daily and cumulative release over 30 days are presented in Tables 2 and 3 and show sustained release over 28 days.

TABLE 2

Daily release of HIV mAb 2F5 from vaginal rings containing a single insert. 2F5 loading = 7.5%, water-soluble release enhancer (glycine) at a loading of 22.5% w/w.

| Time (days) | 2F5 Daily Release (µg) |
|---|---|
| 1 | 1.42 |
| 2 | 1.67 |
| 3 | 1.67 |

TABLE 2-continued

Daily release of HIV mAb 2F5 from vaginal rings containing a single insert. 2F5 loading = 7.5%, water-soluble release enhancer (glycine) at a loading of 22.5% w/w.

| Time (days) | 2F5 Daily Release (µg) |
|---|---|
| 4 | 1.10 |
| 7 | 3.22 |
| 11 | 7.69 |
| 14 | 2.89 |
| 18 | 2.61 |
| 21 | 4.71 |
| 25 | 3.17 |
| 28 | 2.66 |

TABLE 3

Cumulative release of HIV mAb 2F5 from vaginal rings containing a single insert. 2F5 loading = 7.5%, water-soluble release enhancer (glycine) at a loading of 22.5% w/w.

| Time (days) | 2F5 Cumulative Release (µg) |
|---|---|
| 1 | 1.42 |
| 2 | 3.08 |
| 3 | 4.75 |
| 4 | 5.85 |
| 7 | 15.52 |
| 11 | 46.29 |
| 14 | 54.95 |
| 18 | 65.40 |
| 21 | 79.54 |
| 25 | 92.22 |
| 28 | 100.19 |

EXAMPLE 3

Sustained Release of the HIV Envelope Protein gp140 from Intravaginal Drug Delivery Devices Silicone elastomer vaginal rings containing a single channel were manufactured according to the general method described above. Silicone elastomer inserts containing the HIV envelope protein gp140 were prepared as follows. A solid mixture containing gp140 and glycine (weight ratio 2:98) was prepared by freeze-drying a gp140/glycine buffer solution. Uncovered silicone inserts were manufactured by mixing, in a 50:50 weight ratio, the gp140-glycine mix with silicone elastomer (LSR-9-9508-30, 50% w/w) (Dow Corning) in a DAC 150 FVZ-K Speedmixer for 30 seconds at 3000 rpm. The final insert contained gp140, glycine and silicone elastomer in the weight ratio of 1:49:50. The mixture was then inserted into a 2 ml syringe and manually injected into PVC tubing of 3 mm diameter and allowed to cure for 24 hours at room temperature. After this time, the inserts were cut into 9 mm lengths, and the PVC sheath carefully removed from the cured silicone elastomer inserts using a scalpel. A single insert was then placed into the single channel of a vaginal ring device. In vitro daily and cumulative release data over 28 days are presented in Tables 4 and 5.

TABLE 4

Daily release data of gp140 from vaginal rings containing a single insert. gp140 loading = 1.0% w/w; water-soluble release enhancer (glycine) at a loading of 49.0% w/w.

| Time (days) | gp140 Daily Release (µg) |
|---|---|
| 1 | 64.50 |
| 2 | 16.13 |
| 3 | 12.43 |
| 4 | 10.50 |
| 7 | 10.28 |
| 11 | 6.71 |
| 14 | 1.70 |
| 18 | 1.86 |
| 21 | 1.28 |
| 25 | 1.30 |
| 28 | 1.90 |

TABLE 5

Cumulative release data of gp140 from vaginal rings containing a single insert. gp140 = loading 1% w/w; water-soluble release enhancer (glycine) at a loading of 49% w/w.

| Time (days) | gp140 Cumulative Release (µg) |
|---|---|
| 1 | 64.50 |
| 2 | 80.63 |
| 3 | 93.05 |
| 4 | 103.55 |
| 7 | 134.38 |
| 11 | 161.20 |
| 14 | 166.30 |
| 18 | 173.75 |
| 21 | 177.58 |
| 25 | 182.78 |
| 28 | 188.48 |

Protocol for In Vitro Release Studies—Examples 4-6

The drug delivery devices were placed into sample vials with 10 ml of sterile water; the vials were capped and placed in an orbital (60 rpm) shaking incubator (Unitron HT Infors) at 37° C. Daily sampling with complete replacement of the release medium (sterile water) was performed for 14 days, followed by twice-weekly sampling/replacement for a further 2 weeks. Rod-shaped drug delivery devices with a single drug-containing insert therein were used for the dissolution studies performed in Examples 4-6. Such drug delivery devices are an accurate representation of release profiles that could be expected, if rod-shaped inserts loaded with erioglaucine, BSA or 2F5 were in situ in a ring-shaped device body, i.e., the drug would only be released from the two open (uncovered) ends of the drug delivery device.

EXAMPLE 4

Influence of Type and Concentration of Water-Soluble Release Enhancer on the Release of Erioglaucine Silicone elastomer LSR9-9508-30 was supplied by NuSil Technology LLC (Carpinteria, USA). This is a two-part platinum-catalyzed silicone elastomer, in which the platinum catalyst is contained within Part B. Erioglaucine was purchased from Sigma-Aldrich (Gillingham, UK). Ultra-pure water was obtained using an Elga Purelab Maxima system. Medical grade silicone tubing with an internal diameter of 3.35 mm and an external diameter of 4.64 mm was purchased from BDH (Belfast, UK). Erioglaucine has a water solubility of more than 20% w/w at pH 5 and a molecular weight of 793 Da.

Erioglaucine-containing insert formulations were prepared as detailed in Table 6 below. A total 2 g mass was employed for each erioglaucine/water-soluble release enhancer/silicone formulation. The rod-shaped drug delivery devices were manufactured by first mixing the appropriate constituents (i.e., erioglaucine, part A and B silicone elastomer and the water-soluble release enhancer) in the desired concentrations in a DAC 150 FVZ-K Speedmixer for 30 seconds at 3000 rpm. This mixture was then taken up into a syringe and injected into the above-mentioned silicone tubing (length 100 mm, internal diameter 3.35 mm). The tubes were left to cure at room temperature for 24 hours, after which time they were cut into 15 mm length portions, each length being a rod-shaped drug delivery device.

Released erioglaucine concentrations were quantified using a Biotek Powerwave Microplate reader with a detection wavelength of 630 nm, using KC junior software. A linear calibration plot for erioglaucine was obtained over the range 100 ng/ml – 100 μg/ml ($R^2$=0.997).

Figure 2:
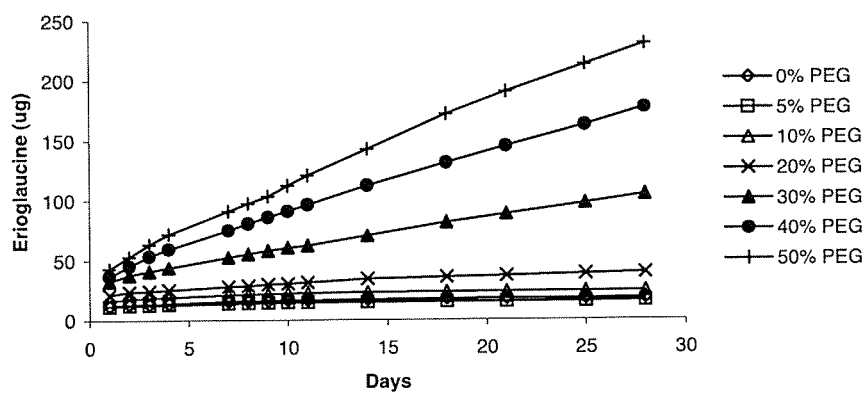
FIG. 2 shows in vitro mean cumulative release profiles of erioglaucine from devices of the present invention with water-soluble release enhancer loadings (○) 0% PEG, (□) 5% PEG, (Δ) 10% PEG (x) 20% PEG (▲) 30% PEG, (●) 40% PEG and (+) 50% PEG (formulations 1, 8, 9, 10, 11, 12, and 13, respectively).
Figure 3:
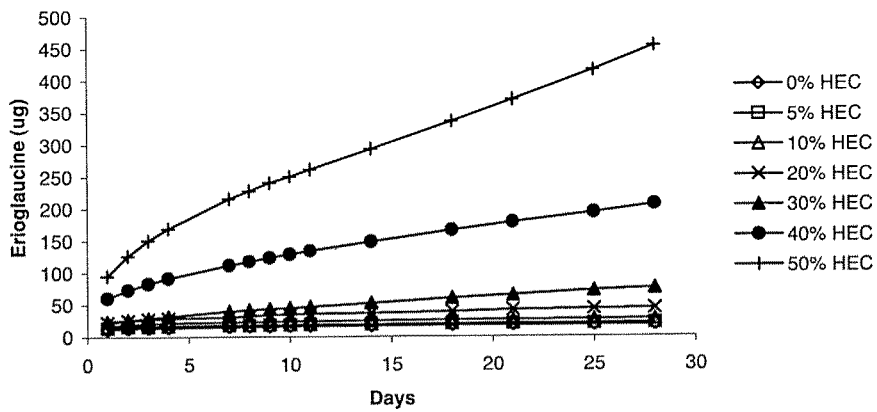
FIG. 3 shows in vitro mean cumulative release profiles of erioglaucine from devices of the present invention with water-soluble release enhancer loadings (○) 0% HEC, (□) 5% HEC, (Δ) 10% HEC (x) 20% HEC (▲) 30% HEC, (●) 40% HEC and (+) 50% HEC (formulations 1, 20, 21, 22, 23, 24, and 25, respectively).

Erioglaucine was continuously released from covered silicone rod formulations possessing a variety of different water-soluble release enhancers at a range of water-soluble release enhancer loadings (Table 6) for a period of 4 weeks. The water-soluble release enhancers were selected on the basis of their low toxicity and for their physicochemical differences; ranging from a simple sugar (glucose), a simple amino acid (glycine), a relatively high molecular weight protein (bovine serum albumin, BSA) and two polymeric compounds of different molecular weights (polyethylene glycol, MW: 3,500—referred to herein as PEG) and hydroxyethylcellulose (MW: 90,000—referred to herein as HEC). FIGS. 2 and 3 illustrate typical release profiles of erioglaucine from rod-shaped drug delivery devices with a single erioglaucine-containing insert contained therein with 0, 5, 10, 20, 30, 40 and 50% loadings of PEG and HEC as water-soluble release enhancers in the insert. The FIGS. 2 and 3 data indicate, when low concentrations of water-soluble release enhancer are included in the formulation (5-10%), only small, or no, improvements in the daily release of erioglaucine are afforded, when compared to rods with no water-soluble release enhancer (0%). It is only when the water-soluble release enhancer concentrations are increased to 20% and above that increases in the daily release are observed. The release rates of erioglaucine from the various formulations were linear over the 4-week study.

Figure 4:
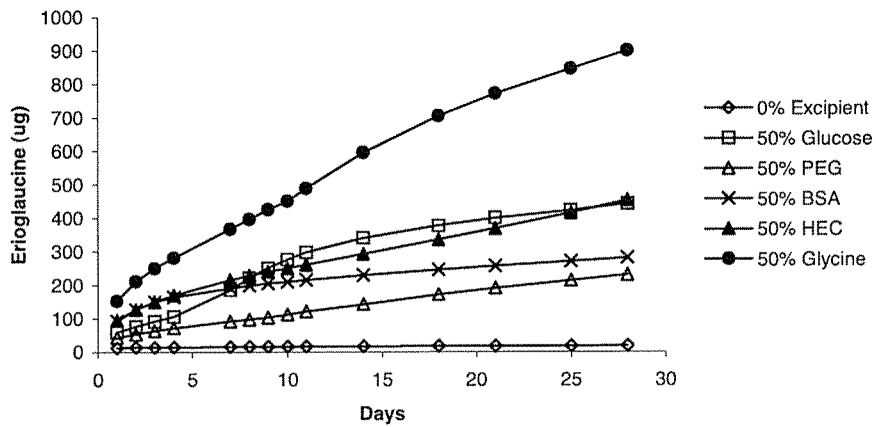
FIG. 4 shows in vitro mean cumulative release profiles of erioglaucine from devices of the present invention with water-soluble release enhancers (○) No water-soluble release enhancer (□) 50% glucose, (Δ) 50% PEG (x) 50% BSA (▲) 50% HEC, (●) 50% glycine (formulations 1, 7, 13, 19 and 25 and 31, respectively).

FIG. 4 shows the cumulative release of erioglaucine from rod-shaped drug delivery devices with a single erioglaucine-containing insert contained therein that include the five different water-soluble release enhancers at 50% loadings. It is clear that glycine offers the highest release enhancing properties over all the other water-soluble release enhancers studied. Glycine provides double the cumulative release of BSA after 28 days compared to the next best water-soluble release enhancer, HEC. Glycine is a preferred water-soluble release enhancer.

TABLE 6

Erioglaucine Formulations.

| No. | Active Name | Drug Loading (% w/w) | Dimensions Length/Internal CSD* (mm) | Water-soluble release enhancer (Name, % w/w) | Dimensions Outer CSD* (mm) |
|---|---|---|---|---|---|
| 1 | Erioglaucine | 1 | 15/3.35 | — | 4.64 |
| 2 | Erioglaucine | 1 | 15/3.35 | D-Glucose, 5 | 4.64 |
| 3 | Erioglaucine | 1 | 15/3.35 | D-Glucose, 10 | 4.64 |
| 4 | Erioglaucine | 1 | 15/3.35 | D-Glucose, 20 | 4.64 |
| 5 | Erioglaucine | 1 | 15/3.35 | D-Glucose, 30 | 4.64 |
| 6 | Erioglaucine | 1 | 15/3.35 | D-Glucose, 40 | 4.64 |
| 7 | Erioglaucine | 1 | 15/3.35 | D-Glucose, 50 | 4.64 |
| 8 | Erioglaucine | 1 | 15/3.35 | PEG, 5 | 4.64 |
| 9 | Erioglaucine | 1 | 15/3.35 | PEG, 10 | 4.64 |
| 10 | Erioglaucine | 1 | 15/3.35 | PEG, 20 | 4.64 |
| 11 | Erioglaucine | 1 | 15/3.35 | PEG, 30 | 4.64 |
| 12 | Erioglaucine | 1 | 15/3.35 | PEG, 40 | 4.64 |
| 13 | Erioglaucine | 1 | 15/3.35 | PEG, 50 | 4.64 |
| 14 | Erioglaucine | 1 | 15/3.35 | BSA, 5 | 4.64 |
| 15 | Erioglaucine | 1 | 15/3.35 | BSA, 10 | 4.64 |
| 16 | Erioglaucine | 1 | 15/3.35 | BSA, 20 | 4.64 |
| 17 | Erioglaucine | 1 | 15/3.35 | BSA, 30 | 4.64 |
| 18 | Erioglaucine | 1 | 15/3.35 | BSA, 40 | 4.64 |
| 19 | Erioglaucine | 1 | 15/3.35 | BSA, 50 | 4.64 |
| 20 | Erioglaucine | 1 | 15/3.35 | HEC, 5 | 4.64 |
| 21 | Erioglaucine | 1 | 15/3.35 | HEC, 10 | 4.64 |
| 22 | Erioglaucine | 1 | 15/3.35 | HEC, 20 | 4.64 |
| 23 | Erioglaucine | 1 | 15/3.35 | HEC, 30 | 4.64 |
| 24 | Erioglaucine | 1 | 15/3.35 | HEC, 40 | 4.64 |
| 25 | Erioglaucine | 1 | 15/3.35 | HEC, 50 | 4.64 |
| 26 | Erioglaucine | 1 | 15/3.35 | Glycine, 5 | 4.64 |
| 27 | Erioglaucine | 1 | 15/3.35 | Glycine, 10 | 4.64 |
| 28 | Erioglaucine | 1 | 15/3.35 | Glycine, 20 | 4.64 |
| 29 | Erioglaucine | 1 | 15/3.35 | Glycine, 30 | 4.64 |
| 30 | Erioglaucine | 1 | 15/3.35 | Glycine, 40 | 4.64 |
| 31 | Erioglaucine | 1 | 15/3.35 | Glycine, 50 | 4.64 |

Table 6a. In vitro cumulative release data of erioglaucine with BSA.

| Time (Days) | 0% BSA | 5% BSA | 10% BSA | 20% BSA | 30% BSA | 40% BSA | 50% BSA |
|---|---|---|---|---|---|---|---|
| 1 | 11.80 | 18.70 | 22.93 | 25.11 | 22.16 | 60.47 | 92.09 |
| 2 | 13.12 | 20.38 | 24.66 | 27.76 | 26.70 | 78.64 | 126.07 |
| 3 | 13.51 | 21.21 | 25.41 | 28.96 | 30.03 | 91.01 | 149.05 |
| 4 | 13.94 | 21.97 | 26.00 | 30.32 | 32.40 | 100.15 | 163.75 |
| 7 | 15.58 | 22.80 | 27.68 | 32.56 | 37.67 | 119.10 | 190.72 |
| 8 | 15.77 | 23.03 | 28.03 | 33.31 | 38.83 | 124.29 | 197.61 |
| 9 | 15.77 | 23.46 | 28.18 | 33.70 | 40.55 | 129.27 | 204.08 |
| 10 | 16.36 | 23.61 | 28.25 | 34.50 | 41.78 | 133.45 | 209.23 |
| 11 | 16.51 | 23.84 | 28.84 | 35.09 | 42.86 | 137.55 | 214.79 |
| 14 | 16.90 | 24.31 | 29.35 | 36.33 | 45.87 | 148.23 | 229.05 |
| 18 | 17.69 | 24.50 | 29.78 | 37.68 | 49.69 | 160.36 | 245.33 |
| 21 | 17.88 | 25.01 | 34.28 | 39.45 | 52.06 | 168.37 | 256.93 |
| 25 | 17.95 | 25.48 | 35.04 | 40.68 | 54.75 | 178.07 | 270.75 |
| 28 | 18.22 | 25.87 | 35.55 | 42.08 | 56.83 | 185.52 | 280.90 |

Table 6b. In vitro cumulative release data of erioglaucine with glucose.

| Time (Days) | 0% Glucose | 5% Glucose | 10% Glucose | 20% Glucose | 30% Glucose | 40% Glucose | 50% Glucose |
|---|---|---|---|---|---|---|---|
| 1 | 11.80 | 14.42 | 16.44 | 18.70 | 23.37 | 32.72 | 59.26 |
| 2 | 13.12 | 15.50 | 17.72 | 20.74 | 28.96 | 40.01 | 75.58 |
| 3 | 13.51 | 16.05 | 19.04 | 23.03 | 33.26 | 47.38 | 90.57 |
| 4 | 13.94 | 16.68 | 19.63 | 24.99 | 37.12 | 54.78 | 105.15 |
| 7 | 15.58 | 17.40 | 20.78 | 30.54 | 47.07 | 71.43 | 184.91 |
| 8 | 15.77 | 17.71 | 21.38 | 32.23 | 51.09 | 78.99 | 221.32 |
| 9 | 15.77 | 17.81 | 21.93 | 33.38 | 53.65 | 88.10 | 249.98 |
| 10 | 16.36 | 18.00 | 22.16 | 34.78 | 57.43 | 99.21 | 275.33 |
| 11 | 16.51 | 18.11 | 22.31 | 36.10 | 61.09 | 110.05 | 297.06 |
| 14 | 16.90 | 18.46 | 23.22 | 39.88 | 69.79 | 127.18 | 340.28 |
| 18 | 17.69 | 18.73 | 23.69 | 45.71 | 84.53 | 148.34 | 376.56 |
| 21 | 17.88 | 19.32 | 24.56 | 51.06 | 99.48 | 165.26 | 399.54 |
| 25 | 17.95 | 19.87 | 25.32 | 58.31 | 112.17 | 184.37 | 422.23 |
| 28 | 18.22 | 20.59 | 25.83 | 62.45 | 121.28 | 199.88 | 441.37 |

Table 6c. In vitro cumulative release data of erioglaucine with glycine.

| Time (Days) | 0% Glycine | 5% Glycine | 10% Glycine | 20% Glycine | 30% Glycine | 40% Glycine | 50% Glycine |
|---|---|---|---|---|---|---|---|
| 1 | 11.80 | 17.49 | 12.69 | 7.49 | 44.18 | 81.68 | 152.66 |
| 2 | 13.12 | 18.16 | 13.97 | 13.69 | 60.33 | 110.99 | 210.24 |

TABLE 6-continued

Erioglaucine Formulations.

| 3 | 13.51 | 18.55 | 14.80 | 18.83 | 75.65 | 135.94 | 249.35 |
| 4 | 13.94 | 18.90 | 15.43 | 24.19 | 86.93 | 156.62 | 280.47 |
| 7 | 15.58 | 19.57 | 17.11 | 42.93 | 110.34 | 212.06 | 367.08 |
| 8 | 15.77 | 19.80 | 18.07 | 48.03 | 126.18 | 227.33 | 396.15 |
| 9 | 15.77 | 20.11 | 18.62 | 53.22 | 128.83 | 239.94 | 424.41 |
| 10 | 16.36 | 20.46 | 18.89 | 58.25 | 131.72 | 249.52 | 449.64 |
| 11 | 16.51 | 20.85 | 19.32 | 63.72 | 135.62 | 261.13 | 488.18 |
| 14 | 16.90 | 21.81 | 21.04 | 77.66 | 151.46 | 293.46 | 595.00 |
| 18 | 17.69 | 22.68 | 23.65 | 97.53 | 171.85 | 330.95 | 703.88 |
| 21 | 17.88 | 23.84 | 26.14 | 112.36 | 190.23 | 358.89 | 770.53 |
| 25 | 17.95 | 24.43 | 29.11 | 133.68 | 218.97 | 398.11 | 845.17 |
| 28 | 18.22 | 25.10 | 31.19 | 145.61 | 242.23 | 426.86 | 899.00 |

Table 6d. In vitro cumulative release data of erioglaucine with HEC.

| Time (Days) | 0% HEC | 5% HEC | 10% HEC | 20% HEC | 30% HEC | 40% HEC | 50% HEC |
| --- | --- | --- | --- | --- | --- | --- | --- |
| 1 | 11.80 | 14.10 | 17.01 | 22.37 | 24.09 | 60.87 | 95.07 |
| 2 | 13.12 | 15.74 | 19.49 | 25.02 | 26.50 | 72.88 | 126.19 |
| 3 | 13.51 | 16.25 | 20.81 | 27.30 | 29.07 | 82.46 | 149.89 |
| 4 | 13.94 | 16.93 | 21.48 | 28.62 | 31.79 | 90.84 | 168.96 |
| 7 | 15.58 | 17.92 | 22.68 | 30.91 | 39.44 | 111.51 | 214.92 |
| 8 | 15.77 | 18.07 | 23.11 | 32.23 | 41.17 | 117.27 | 227.21 |
| 9 | 15.77 | 18.34 | 23.46 | 33.66 | 43.53 | 123.18 | 239.70 |
| 10 | 16.36 | 18.69 | 24.13 | 34.90 | 44.93 | 128.29 | 249.64 |
| 11 | 16.51 | 18.76 | 24.32 | 35.45 | 46.49 | 133.68 | 260.36 |
| 14 | 16.90 | 19.03 | 24.75 | 36.73 | 52.32 | 147.95 | 292.25 |
| 18 | 17.69 | 19.58 | 25.46 | 38.73 | 60.18 | 165.36 | 335.39 |
| 21 | 17.88 | 20.13 | 25.85 | 41.38 | 64.72 | 178.05 | 369.05 |
| 25 | 17.95 | 20.36 | 26.81 | 42.90 | 71.52 | 193.24 | 414.53 |
| 28 | 18.22 | 20.59 | 27.16 | 43.90 | 75.26 | 205.49 | 452.51 |

Table 6e. In vitro cumulative release data of erioglaucine with PEG.

| Time (Days) | 0% PEG | 5% PEG | 10% PEG | 20% PEG | 30% PEG | 40% PEG | 50% PEG |
| --- | --- | --- | --- | --- | --- | --- | --- |
| 1 | 11.80 | 11.44 | 16.44 | 21.20 | 32.40 | 36.84 | 42.80 |
| 2 | 13.12 | 12.19 | 17.60 | 23.45 | 37.59 | 45.17 | 52.79 |
| 3 | 13.51 | 12.54 | 18.55 | 24.24 | 41.04 | 53.34 | 63.43 |
| 4 | 13.94 | 12.85 | 19.06 | 25.07 | 43.77 | 59.30 | 71.80 |
| 7 | 15.58 | 13.81 | 20.87 | 27.96 | 52.23 | 74.85 | 90.78 |
| 8 | 15.77 | 14.04 | 21.46 | 28.60 | 55.08 | 80.57 | 97.14 |
| 9 | 15.77 | 14.35 | 21.65 | 29.55 | 57.97 | 85.68 | 103.02 |
| 10 | 16.36 | 14.49 | 22.36 | 30.06 | 60.17 | 90.70 | 112.08 |
| 11 | 16.51 | 14.60 | 22.71 | 31.22 | 62.22 | 96.06 | 120.45 |
| 14 | 16.90 | 14.83 | 23.10 | 34.03 | 70.23 | 112.13 | 142.38 |
| 18 | 17.69 | 15.06 | 23.41 | 35.67 | 81.23 | 130.91 | 171.41 |
| 21 | 17.88 | 15.17 | 23.64 | 36.78 | 88.39 | 144.49 | 190.02 |
| 25 | 17.95 | 15.40 | 23.83 | 38.02 | 97.17 | 162.10 | 212.76 |
| 28 | 18.22 | 15.67 | 24.05 | 39.18 | 104.22 | 176.65 | 229.84 |

*CSD is cross sectional diameter.

The dissolution studies involving erioglaucine (FIGS. 2, 3 and 4) illustrate the extent to which the release of a hydrophilic, macromolecular drug from a hydrophobic insert carrier material can be influenced. As mentioned above, erioglaucine is water-soluble, i.e. has a solubility in water of greater than 5% w/w and is macromolecular. It is clear from these data that erioglaucine does not diffuse through the silicone insert carrier material without the aid of the water-soluble release enhancer(s) dispersed throughout the insert carrier material. Where a water-soluble release enhancer was excluded from the formulation of the insert carrier material (i.e., 0% loading), there is only low surface release of erioglaucine over the first few days, after which time erioglaucine concentrations are extremely low.

It is thought that the poor diffusion/permeation of erioglaucine is due to both the relatively low solubility and the relatively high molecular weight of erioglaucine (relative to molecules that typically diffuse through the silicone insert carrier materials —<400 Daltons), thereby inhibiting its ability to diffuse through the exemplified silicone insert carrier material that is hydrophobic.

It is also evident that small (5 and 10%) additions of water-soluble release enhancers to the drug-containing inserts have little effect on enhancing the release of erioglaucine. Only when water-soluble release enhancer concentrations reach 15 or 20% and above, is the release rate enhanced significantly. At 20, 30, 40 and 50% PEG loadings, the cumulative release of erioglaucine is enhanced by 2, 6, 10 and 13 fold, respectively, by the end of the 28-day study. In the case of HEC, the cumulative release of erioglaucine is enhanced 2, 4, 11 and 25 fold, respectively, by the end of the 28-day study. It is, therefore, beneficial to maintain the highest water-soluble release enhancer loadings as possible (such as, for example, 50%). This improved release of erioglaucine is thought to be caused by increased water uptake into the hydrophobic medium of the insert carrier material, due to the presence of the water-soluble release enhancer. This is thought to create a series of interconnecting channels and pores through which dissolution medium and erioglaucine can move and thus diffuse from the drug delivery devices of the present invention.

Figure 11A:
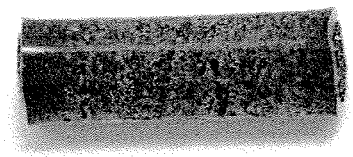
FIG. 11 shows erioglaucine devices of the present invention loaded with (1) 50% PEG and (2) 50% glycine, after 28 days of dissolution.
Figure 11B:
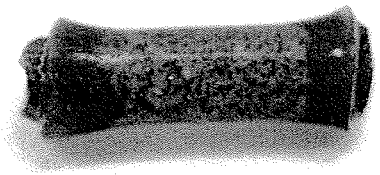

All the water-soluble release enhancers examined herein were shown to affect the release of erioglaucine in a concentration dependent manner. The only difference between the different water-soluble release enhancers is the magnitude in which they enhanced erioglaucine release. FIG. 4 illustrates the release of erioglaucine from rod-shaped drug delivery devices with a single erioglaucine-containing insert contained therein with a range of water-soluble release enhancers at 50% loadings. It is apparent that glycine, D-glucose and HEC offered the greatest improvement in the release of erioglaucine, of which glycine offered the greatest improvement in the release of erioglaucine. The improved release with glycine is most probably related to the increased swelling of the rod-shaped drug delivery devices with this water-soluble release enhancer, as shown in FIGS. 11A and 11B. This image of the 50% PEG rod (FIG. 11A) is typical of all the water-soluble release enhancers after 28 days of dissolution, except glycine (FIG. 11B), where zero to minimal swelling of the rod-shaped drug delivery device is visible. In the case of glycine, the additional swelling of the rod-shaped drug delivery devices results in the polymer network expanding further, thereby creating an increased number of pores and voids through which dissolution media and erioglaucine can move.

The studies involving erioglaucine illustrate how macromolecular but moderately low molecular weight hydrophilic drugs can be delivered from silicone inserts in high concentrations by the inclusion of water-soluble release enhancers. These studies were extended (see Example 5 below) to examine the release of a model protein, BSA, from similar rod-shaped drug delivery devices.

EXAMPLE 5

Influence of Excipient Concentration on BSA Release Profiles

Silicone elastomer LSR9-9508-30 was supplied by NuSil Technology LLC (Carpinteria, USA). BSA was purchased from Sigma-Aldrich (Gillingham, UK). Ultra-pure water was obtained using an Elga Purelab Maxima system. Medical grade silicone tubing with an internal diameter of 3.35 mm and an external diameter of 4.64 mm was purchased from BDH (Belfast, UK)

BSA-containing insert formulations were prepared as detailed in Table 7 below. A total 2 g mass was employed for each BSA/water-soluble release enhancer/silicone formulation. The rod-shaped drug delivery devices were manufactured by first mixing the appropriate constituents (i.e., BSA, part A and B silicone elastomer and the water-soluble release enhancer) in the desired concentrations in a DAC 150 FVZ-K Speedmixer for 30 seconds at 3000 rpm. This mixture was then taken up into a syringe and injected into silicone tubing (length 100 mm, internal diameter 3.35 mm). The tubes were left to cure at room temperature for 24 hours, after which time they were cut into 15 mm length portions, each length being a rod-shaped drug delivery device.

TABLE 7

BSA Formulations.

| No. | Active Name | Drug Loading (% w/w) | Dimensions Length/ Internal CSD (mm) | Glycine (% w/w) | Dimensions Outer CSD (mm) |
|---|---|---|---|---|---|
| 32 | BSA | 1 | 15/3.35 | — | 4.64 |
| 33 | BSA | 1 | 15/3.35 | 30 | 4.64 |
| 34 | BSA | 1 | 15/3.35 | 40 | 4.64 |
| 35 | BSA | 1 | 15/3.35 | 50 | 4.64 |

BSA released from rod-shaped drug delivery devices with a single BSA-containing insert contained therein was quantified using size exclusion high performance liquid chromatography with ultraviolet detection (Waters Breeze HPLC system; Phenomenex Biosep SECS 3000 column 7.8 mm i.d×300 mm; with Security guard cartridge GFC 3000 4×3.0 mm; run temperature 25° C.; isocratic mode; mobile phase ammonium acetate/0.01 M pH 6.8; flow rate 1.0 ml/min; detection wavelength 280 nm; injection volume 100 µl; BSA retention time 7.6 min). A linear calibration plot for BSA was obtained over the range 0.5-100 µg/ml ($R^2$=0.98).

Figure 5:
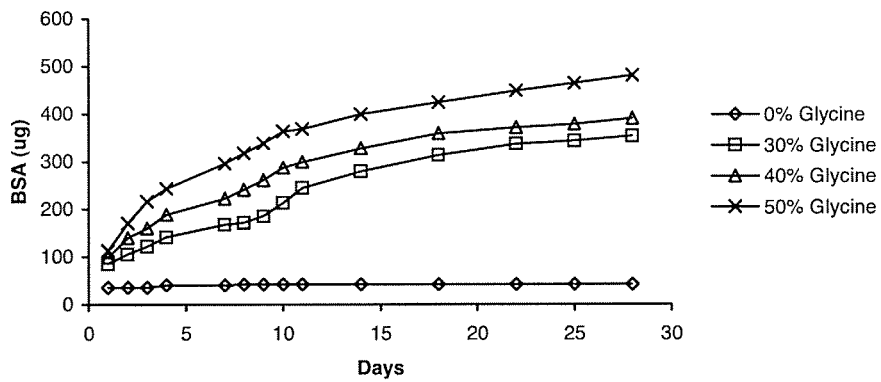
FIG. 5 shows in vitro mean cumulative release profiles of BSA from devices of the present invention with water-soluble release enhancers (○) No water-soluble release enhancer, (□) 30% glycine, (Δ) 40% glycine (x) 50% glycine (formulations 32, 33, 34 and 35, respectively).
Figure 6:
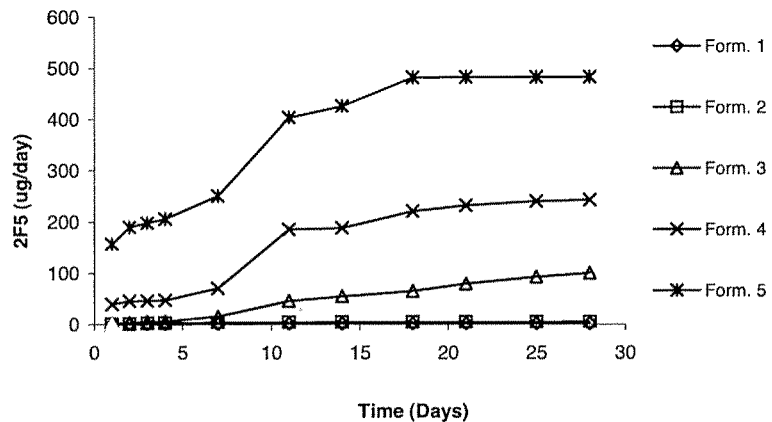
FIG. 6 shows the effect of 2F5 loading on release profile via in vitro cumulative release of 2F5 from devices of the present invention with 30% water-soluble release enhancer loadings.
Figure 7:
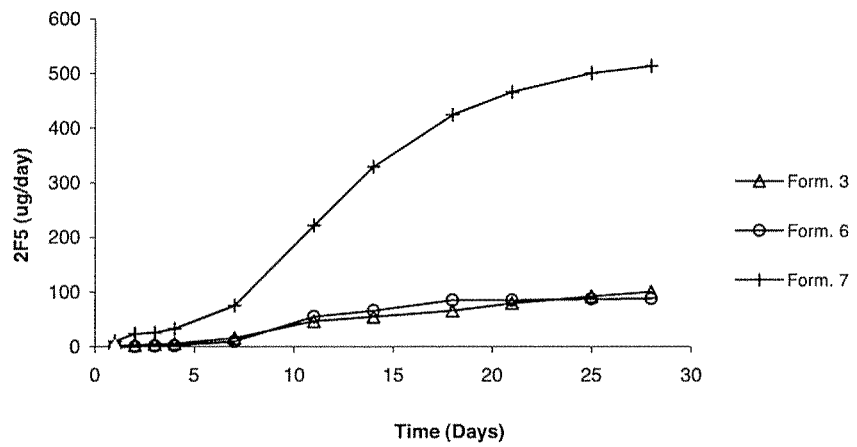
FIG. 7 shows the effect of silicone elastomer type and excipient/elastomer loading ratio via in vitro cumulative release of 2F5 from devices of the present invention with 30% water-soluble release enhancer loadings.
Figure 8:
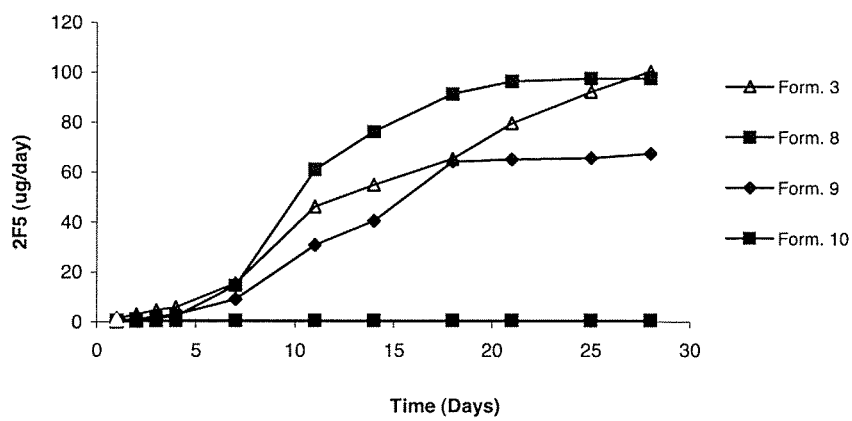
FIG. 8 shows the effect of curing conditions via in vitro cumulative release of 2F5 from devices of the present invention with 30% water-soluble release enhancer loadings.

BSA was continuously released from rod-shaped drug delivery devices with a single BSA-containing insert contained therein possessing 0, 30, 40 and 50% glycine loadings. FIG. 5 demonstrates that BSA diffuses poorly from rod-shaped drug delivery devices without the incorporation of glycine in the formulation—BSA is only released at low concentrations for the first few days from the surface of the rod-shaped drug delivery devices. The inclusion of glycine in the insert formulations at 30, 40 and 50% affords 9, 10 and 12 fold increases in the cumulative release of BSA over a 4-week period.

In the case of BSA, the dissolution studies were performed using only glycine as the water-soluble release enhancer, and the loadings were maintained above 30%. The data obtained (FIG. 5) indicate that, despite the significant increase in molecular weight of BSA compared to erioglaucine, considerable concentrations of BSA can be delivered from the rod-shaped drug delivery devices for prolonged periods. At 50% loadings of glycine, a single rod-shaped drug delivery device will provide up to 480 µg of BSA over a 28-day period.

With this in mind, such modified silicone rod-shaped drug delivery devices have the ability to deliver high, localized concentrations of vaginal antibodies for prolonged periods, which could offer vaginal protection against HIV. Hence, experiments were performed with the objective of producing a model rod-shaped drug delivery device for effective prolonged delivery of monoclonal antibodies such as 2F5 from rod insert vaginal rings (see Example 6 below).

EXAMPLE 6

Influence of Excipient Concentration, 2F5 Concentration and Manufacturing and Processing Parameters on the Release of 2F5

2F5 was kindly provided by Polymun Scientific (Vienna, Austria). Silicone elastomer LSR9-9508-30 was supplied by NuSil Technology LLC (Carpinteria, USA). Ultra-pure water was obtained using an Elga Purelab Maxima system. Medical grade silicone tubing with an internal diameter of 3.35 mm and an external diameter of 4.64 mm was purchased from BDH (Belfast, Uk)

Formulations were prepared as detailed in Table 8. A total 1 g mass was employed for each 2F5/silicone/water-soluble release enhancer formulation.

TABLE 8

2F5 Formulations with 30% Drug Plus Water-Soluble Release Enhancer Loading.

| No. | Silicone Elastomer (Type, Amount % w/w) | Drug - 2F5 (Prep., Loading % w/w) | Glycine Loading % (w/w) | Curing Conditions (Temp., Duration) |
|---|---|---|---|---|
| Effect of 2F5 Loading | | | | |
| 1 | Platinum A, 70 | Freeze Dry A, 1.5 | 28.5 | ambient, overnight |
| 2 | Platinum A, 70 | Freeze Dry A, 3.75 | 26.25 | ambient, overnight |
| 3 | Platinum A, 70 | Freeze Dry A, 7.5 | 22.5 | ambient, overnight |
| 4 | Platinum A, 70 | Freeze Dry A, 15.0 | 15.0 | ambient, overnight |
| 5 | Platinum A, 70 | Freeze Dry A, 22.5 | 7.5 | ambient, overnight |
| Effect of Excipient Loading | | | | |
| 6 | Platinum A, 80 | Freeze Dry A, 7.5 | 12.5 | ambient, overnight |
| Effect of Silicone Elastomer | | | | |
| 7 | Platinum B, 70 | Freeze Dry A, 7.5 | 22.5 | ambient, overnight |
| Effect of Silicone Elastomer Curing Conditions | | | | |
| 8 | Platinum A, 70 | Freeze Dry A, 7.5 | 22.5 | 40° C., 8 hrs |
| 9 | Platinum A, 70 | Freeze Dry A, 7.5 | 22.5 | 70° C., 4 hrs |
| 10 | Platinum A, 70 | Freeze Dry A, 7.5 | 22.5 | 100° C., 1 hour |
| Controls | | | | |
| 11 | Platinum A, 70 | — | 30 | ambient, overnight |
| 12 | Platinum A, 100 | — | — | ambient, overnight |

Two different platinum-catalyzed silicone systems of differing viscosity (Type A and B) were used. The silicone elastomer system termed Platinum A is Nusil's LSR9-9508-30, a two-part addition-cure liquid silicone rubber, each part having a relatively high viscosity (45,000 and 60,000 cp). The silicone elastomer system termed Platinum B is Nusil's MED-4220, a two-part addition-cure liquid silicone rubber, each part having a relatively low viscosity (20,000 and 15,000 cp).

Formulations 1-12: Aqueous solutions of 2F5 (13.54 mg/ml) were mixed with the total quantity of glycine to be included in the final 1 g formulation. Where the total volume of liquid was less then 15 ml, excess water was added to make up this volume to ensure complete dissolution of the glycine. These solutions were lyophilized using a laboratory freeze-dryer (VirTis adVantage). Samples were loaded onto the shelf at room temperature. The shelf temperature was ramped to −60° C. and held for 2 hours. Primary drying was conducted at −30° C. for 15 hours. The shelf temperature was then increased to 20° C. within 60 minutes and held at this temperature for 10 hours. Chamber pressure was controlled at 100 millitorr throughout the drying cycle. After lyophilization, the dried material was mixed with the appropriate quantity of silicone in a DAC 150 FVZ-K Speedmixer for 30 seconds at 3000 rpm. The mixture was taken up into a syringe (2 ml) and injected into silicone tubing (length 100 mm, internal diameter 3.35 mm). The tubes were left to cure at room temperature for 24 hours after which time they were cut into 15 mm length portions. Formulations 11 and 12 (the controls) excluded 2F5, and formulation 12 also excluded glycine.

Table 8 details a series of 2F5 formulations that assess a range of manufacturing and processing parameters on the release of 2F5 from silicone rod inserts. For all of formulations 1-12, the total loading of insert drug and water-soluble release enhancer (2F5+ glycine) remains the same (30% w/w), except for formulation 6 where a 20% loading of insert drug and water-soluble release enhancer was employed.

Quantification of release of 2F5 by ELISA assay: 2F5 levels were quantified by a double-sandwich ELISA using the 2F5 antibody and the peptide aa:GGGLELDKWASL (SEQ ID 1) as the capture antigen. The standard solution was diluted to a concentration of 200 ng/ml for detection of plasma Ab. Bound 2F5 was detected with goat anti-human (GAH) IgG (γ-chain specific) antibody conjugated with horseradish peroxidase. TMBE was added as substrate and optical density values of the formed blue colored product were obtained at 450 nm.

The data presented (FIGS. 6-8) show the release of 2F5 from rod-shaped drug delivery devices having a single 2F5-containing insert therein from a range of experiments (Table 8) that aimed to examine the effects of processing and manufacturing variables on the release of 2F5. 2F5 was continuously released from all the formulations for a period of 28 days. The two controls, formulations 11 and 12, did not produce any interference with the 2F5 ELISA assay.

Formulations 1-5 examine the effect of increasing concentration of 2F5 on the release profile (see FIG. 6). As release of 2F5 from rod-shaped drug delivery devices is exclusively from the two uncovered ends of the rods (2F5 will not diffuse through the device body comprising silicone as the hydrophobic carrier material), it would be expected that, as the loadings of 2F5 increase from 1.5% up to 22.5%, so the release of 2F5 would increase (Kajhara et al. 2001). In fact, although it may be difficult to accurately model the release of 2F5 from these systems as the release is affected by both diffusion out of the rod-shaped drug delivery devices and the uptake of water into the system, and by both the concentration of 2F5 and glycine in the systems, it may be expected that, as 2F5 concentration increases, so the daily release should increase in a linear fashion. However, the results indicate that, as the 2F5 loading increases, the daily release increases considerably more than in a directly proportionate manner. Both of formulation 6 and formulation 3 have the same 2F5 loading, but the relative glycine loading is less for Formulation 6. As a result, the relative insert carrier material loading is increased to compensate (see FIG. 7). In the case of formulation 6, the overall excipient concentration was reduced to 20%, however, the release profile was similar to formulation 3 where the 2F5 concentration was the same, but the glycine loading 10% higher. Formulation 7 involved the use of a different insert carrier material (silicone elastomer (MED 4220, Nusil)) compared to all the other formulations tested. This formulation afforded the highest cumulative release of 2F5 over the 28-day study. However, these data are not a true representation of MED 4220, as this polymer did not cure fully with the inclusion of 2F5 and glycine in the elastomer mix (see FIG. 7). In experiment 7, where a different polymer was employed in the rod-shaped drug delivery device (MED 4220, Nusil), a significant five fold increase in the cumulative release of 2F5 over the 28-day period can be observed when compared to a similar formulation (formulation 3) with silicone A (LSR9-9508-30). However, silicone B (MED 4220) does not cure in the presence of high loadings of lyophilized glycine powders and, therefore, this silicone could not be employed as viable insert carrier material, when the water-soluble release enhancer is glycine. Nevertheless, this considerable increase in 2F5 release caused by the lower density of the uncured silicone network, which affords a more direct pathway for 2F5 diffusion, suggests that 2F5 release can be enhanced by lowering the density of the silicone employed. For this reason, similar rod-shaped drug delivery devices with a single 2F5-containing insert contained therein are examined, in which the polymer network density is reduced by the inclusion of liquid polydimethoxysilane in the formulation—see Examples 7 and 8 below.

Formulations 8-10 (Table 8) examine the effect of the cure temperature of the insert carrier material (for example, silicone elastomer formulations) on the release of 2F5 (see FIG. 8). The release data indicate that increasing the curing temperature to 40° C. for an 8-hour period (formulation 8) had no significant effect on the release of 2F5, i.e., a similar release profile to the comparable formulation 3, which was cured at room temperature. Where the cure temperature was increased to 70° C. for 4 hours (formulation 9), the release of 2F5 after the 28 day period of the study was approximately 35% lower than similar formulations cured at room temperature and 40° C. (formulations 3 and 8, respectively). Where the cure temperature was increased to 100° C. for one hour (formulation 10), only extremely low levels of 2F5 was detected for the first few days of the study.

Experiments 8-10 examine the effect of cure temperature on the release of 2F5, which ultimately offers some indication of 2F5 stability at these temperatures. Ordinarily, the curing of many silicone insert carrier materials, such as those employed herein, is performed at elevated temperatures for a short time—usually above 100° C. for a few minutes. There are, however, obvious concerns with antibody stability when using such elevated temperatures. For this reason, the majority of the drug-containing inserts were cured at room temperature, which prolongs the curing time to several hours. It would, however, be more practical to find optimal curing conditions for such systems that maintain the stability of the drug, while allowing the insert carrier material to cure in as short a time possible.

The release data provided are an indication of the stability of 2F5 at elevated temperatures, although not conclusive. The data show that curing at 40° C. for 8 hours (formulation 8) had no significant effect on the concentrations of 2F5 released from the rod-shaped drug delivery devices, signifying that 2F5 was stable within the silicone insert carrier material at this temperature. When the temperature of curing was increased to 70° C. for a period of 4 hours (formulation 9), the release of 2F5 after the 28-day period of the study was approximately 35% lower than similar formulations cured at room temperature and 40° C. (formulations 3 and 8, respectively). When the curing temperature was increased to 100° C. for one hour, only extremely low levels of 2F5 were detected for the first few days of the study (formulation 10). Surprisingly, therefore, 2F5 is still relatively stable at elevated temperatures approaching 70° C. With further stability testing, an optimized temperature cure and time could be achieved, while still maintaining 100% stability of 2F5.

EXAMPLE 7

Influence of Liquid Polydimethylsiloxane on the Release of 2F5

TABLE 9

2F5 Formulations - comparing the effect of including liquid polydimethylsiloxane (PDMS).

| No. | Silicone Elastomer (Type, Amount % w/w) | 2F5 (Prep., Loading % w/w) | Glycine (Loading % w/w) | Silicone Oil (Loading % w/w) | Curing Conditions (Temp., Duration) |
|---|---|---|---|---|---|
| 1N | Platinum A, 50 | Freeze Dry A, 10 | 40 | 0 | 40° C., 8 hrs |
| 2N | Platinum A, 40 | Freeze Dry A, 10 | 40, | 10% | 40° C., 8 hrs |

2F5 was continuously released from each rod-shaped drug delivery device for a period of 28 days. Liquid PDMS was incorporated into the formulation in order to reduce the polymer network density, which should result in enhanced release of 2F5 from the rod-shaped drug delivery devices. These formulations are not directly comparable to those in Table 8, due a difference in the excipient loadings between the formulations.

Figure 9:
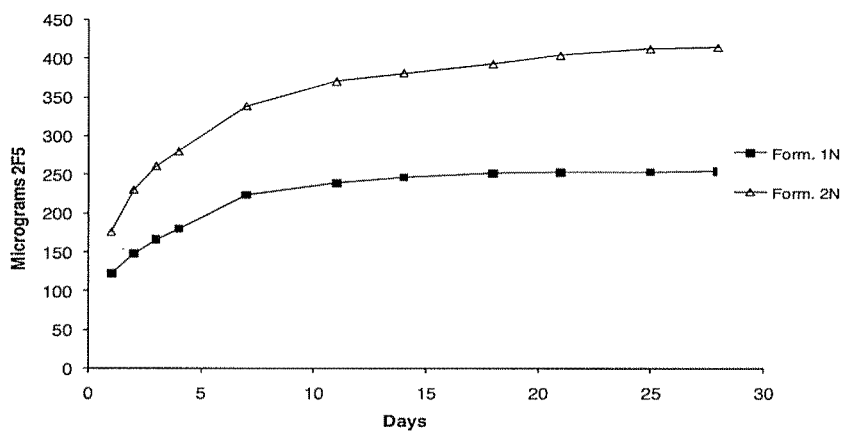
FIG. 9 shows the effect of including liquid polydimethylsiloxane (PDMS) via in vitro cumulative release of 2F5 from devices of the present invention.

FIG. 9 demonstrates that the inclusion of the liquid PDMS in the formulation (formulation 2N) produced a significant enhancement in the cumulative release of 2F5 over a 28 day period, when compared to a similar formulation without liquid PDMS (formulation 1N). The cumulative concentrations at day 28 are 254 µg for those formulations not containing liquid PDMS and 414 µg for those with PDMS included—an increase of over 60%.

The addition of liquid silicone to these formulations has the extra benefit of allowing easier mixing of the solid glycine water-soluble release enhancers into the reduced viscosity elastomer mix. Furthermore, the reduction in the elastomer matrix density allows for a higher loading of glycine, which can further enhance release of the actives. There are thus clear strategies available for further enhancing the release of actives from the drug delivery devices of the present invention.

EXAMPLE 8

Influence of Liquid Polydimethylsiloxane on the Release of BSA

A reduction in the density of the silicone polymer network could improve the diffusion of molecules through the elastomer. One means of reducing the density of the polymer network, aside from using a different polymer, is by the addition of liquid silicone (Polydimethoxysilane—PDMS) to the elastomer. This dilution of the silicone elastomer should also permit the inclusion of a higher portion of solid water-soluble release enhancers into silicone mix, which will also serve to enhance release.

Rod Formulations and Rod Manufacture: Rod-shaped drug delivery devices with a single BSA-containing insert therein were manufactured by mixing the appropriate constituents, as shown in Table 10, (i.e., BSA, Part A and B silicone elastomer, glycine and PDMS, where appropriate) in a DAC 150 Speedmixer at 3000 rpm for 30 seconds. The mixture was taken up into a syringe and injected into silicone tubing (length 100 mm, internal diameter 3.35 mm). The tubes were left to cure at room temperature for 24 hour, after which time they were cut into 15 mm length portions, each length being a rod-shaped drug delivery device.

TABLE 10

BSA Formulations - comparing the effect of including liquid polydimethylsiloxane (PDMS).

| Formulation No. | Drug Name | Drug Loading (% w/w) | Silicone polymer loading (% w/w) | Glycine (% w/w) | PDMS (% w/w) | Rod internal diameter (mm) | No. Rods |
|---|---|---|---|---|---|---|---|
| 1 | BSA | 1% | 50 | 49 | 0 | 3.35 | 1 |
| 2 | BSA | 1% | 40 | 49 | 10 | 3.35 | 1 |
| 3 | BSA | 1% | 30 | 59 | 10 | 3.35 | 1 |

In Vitro Release Studies: Each of the rod-shaped drug delivery devices was placed into a sample vial with 10 ml of water; the vials were capped and placed in an orbital (60 rpm) shaking incubator at 37° C. The rods were placed into new 10 ml volumes of water daily for 2 weeks followed by twice weekly for a further 2 weeks.

Quantification of release of BSA by high performance liquid chromatography: BSA released from rod-shaped drug delivery devices was quantified using size exclusion high performance liquid chromatography with ultraviolet detection (Waters Breeze HPLC system; Phenomenex Biosep SECS 3000 column 7.8 mm i.d×300 mm; with Security guard cartridge GFC 3000 4×3.0 mm; run temperature 25° C.; isocratic mode; mobile phase ammonium acetate/0.01 M pH 6.8; flow rate 1.0 ml/min; detection wavelength 280 nm; injection volume 100 µm; BSA retention time 7.6 min). A linear calibration plot for BSA was obtained over the range 0.5-100 µg/ml ($R^2$=0.98).

TABLE 11

In vitro cumulative release data of BSA (1% loading)(formulations 11, 12 and 13 respectively).

| Time (Days) | 50% Silicone, 49% Glycine Formulation 1(µg) | 40% Silicone, 49% Glycine, 10% PDMS Formulation 2(µg) | 30% Silicone, 59% Glycine, 10% PDMS Formulation 3(µg) |
|---|---|---|---|
| 1 | 101.26 | 101.05 | 221.38 |
| 2 | 131.24 | 134.45 | 279.16 |
| 3 | 158.87 | 160.13 | 377.54 |
| 4 | 187.13 | 190.03 | 427.94 |
| 7 | 241.13 | 225.17 | 520.58 |
| 8 | 258.43 | 237.37 | 559.47 |
| 9 | 271.50 | 246.03 | 594.82 |
| 11 | 286.66 | 259.97 | 656.04 |
| 14 | 305.78 | 277.49 | 726.16 |
| 18 | 335.67 | 309.88 | 798.44 |
| 21 | 364.88 | 357.84 | 898.08 |

TABLE 11-continued

In vitro cumulative release data of BSA (1% loading)(formulations 11, 12 and 13 respectively).

| Time (Days) | 50% Silicone, 49% Glycine Formulation 1(μg) | 40% Silicone, 49% Glycine, 10% PDMS Formulation 2(μg) | 30% Silicone, 59% Glycine, 10% PDMS Formulation 3(μg) |
|---|---|---|---|
| 25 | 381.03 | 392.31 | 958.88 |
| 28 | 393.33 | 441.18 | 1030.96 |

Figure 10:
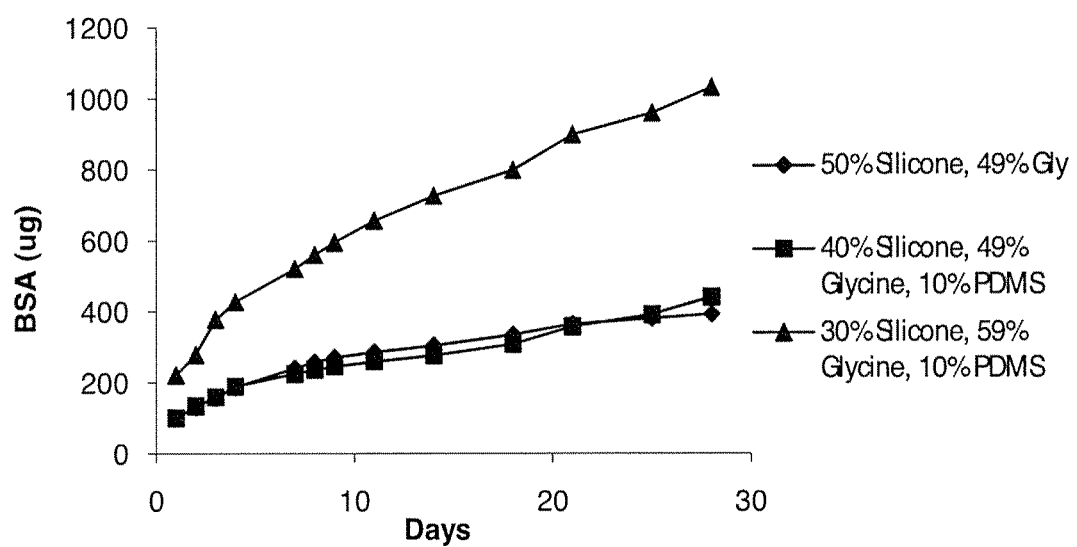
FIG. 10 shows in vitro cumulative release profile of BSA (1% loading) from devices of the present invention containing (♦) 50% silicone, 49% glycine, (□) 40% silicone, 49% glycine, 10% PDMS; (▲) 30% silicone, 59% glycine, 10% PDMS (formulations 11, 12 and 13 respectively).

The data show that the addition of PDMS has some effect on the release profile of BSA from rod-shaped drug delivery devices, but that the release profile is primarily dictated by the amount of glycine as water-soluble release enhancer in the formulation; see FIG. 10. This is confirmed by the fact that those rod-shaped drug delivery devices that contained 49% glycine and PDMS released approximately 12% more BSA over the 28 days, than those devices that contained 49% glycine alone. In addition, PDMS has the added effect of diluting the elastomer enough to allow even higher loadings of water-soluble release enhancers. Therefore, it was possible to easily include 59% glycine loadings into the insert within the rod-shaped drug delivery device with only 30% silicone elastomer, which resulted in substantially enhanced release of BSA.

It is thought that the inclusion of water-soluble release enhancers within the drug-containing insert enhances the drug release by allowing: (i) aqueous fluid to influx into the drug-containing insert, (ii) aqueous solubilization of the drug, and (iii) diffusion of the drug along the aqueous channels and pores formed as a result of imbibation of water.

The optional inclusion of silicone oil in the drug-containing insert serves to dilute the crosslink density of the insert carrier material, since the silicone oil molecules are not capable of being crosslinked into the structure of the insert carrier material. From a practical perspective, we can view the silicone oil molecules as interpenetrating those of the conventional crosslinked network of the insert carrier material. As the loading of the silicone oil component increases (and the loading of the conventional insert carrier material subsequently decreases, the former acting as a substitute for the latter), the rate of diffusion of molecules either into or out of the insert carrier material will increase. Thus, the rate of aqueous fluid uptake increases (due to the more open network structure), and the diffusion of drugs out of the insert carrier material also increases. In other words, it is thought that these are potentially two mechanisms, working together, that operate to enhance the release of drugs from a silicone oil-modified intravaginal drug delivery device of the present invention.

We have demonstrated the potential of the intravaginal drug delivery devices of the present invention as an effective vaginal drug delivery system. Conventional intravaginal drug delivery devices possess a number of beneficial attributes compared to alternative vaginal formulations, including prolonged and controlled drug delivery as well as a considerable improvement in patient compliance. Intravaginal drug delivery devices of the present invention, in addition to retaining the benefits of conventional intravaginal drug delivery devices, possess the added advantage of allowing the delivery of a more diverse range of drugs. Furthermore, they require considerably lower drug loadings, which is of benefit where expensive drugs are employed. Intravaginal drug delivery devices of the present invention, possessing inserts modified with about 1 to about 70% by weight of water-soluble-release enhancers, provide an effective means of delivering potentially any drug to the vagina, including water-soluble drugs and macromolecular drugs.

We have demonstrated the practical application of intravaginal drug delivery devices of the present invention as a viable medium to protect against HIV by achieving prolonged delivery of the vaginal antibody 2F5 from rod-shaped drug delivery devices with a single 2F5-containing insert therein. It has been established that a single insert, rod-shaped drug delivery device with a 22.5% loading of 2F5 will deliver up to 480 μg of 2F5 over a 28-day period (an average of 27 μg/day of 2F5). Considerably higher concentrations of 2F5 could be achieved by positioning two or more drug-containing rod-shaped inserts in a single intravaginal drug delivery device and/or by increasing the diameter of each rod-shaped insert.

The intravaginal drug delivery devices of the present invention, therefore, have the potential to be a leading drug delivery device for the vaginal protection against HIV. It could offer women with the means of protecting themselves discretely without their partners knowing, as vaginal rings can go unnoticed during intercourse. The nature of the drug delivery device of the present invention is such that multiple vaginal antibodies, or alternative microbicidal drugs, could be delivered from a single intravaginal drug delivery device of the present invention with optimized rod-shaped insert formulations for each drug to provide an effective and broad range of protection.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims.

What is claimed is:

1. An intravaginal drug delivery device comprising:
   (a) a device body comprising a hydrophobic carrier material having at least one channel defining at least one opening to an exterior of said device body, said at least one channel being adapted to receive at least one drug-containing insert; and
   (b) at least one drug-containing insert positioned in said at least one channel, said drug-containing insert being capable of releasing a pharmaceutically effective amount of at least one drug suitable for intravaginal administration and containing at least one water-soluble release enhancer in an amount ranging from about 20% to about 70% by weight of said at least one drug-containing insert, said at least one drug and said at least one water-soluble release enhancer being dispersed in an insert carrier material;
   wherein said hydrophobic carrier material and said insert carrier material may be the same or different;
   wherein said at least one drug-containing insert is exposed on said exterior of said device body when said intravaginal drug delivery device is in use;
   wherein said at least one drug-containing insert is arranged to maintain surface contact between said insert and said channel in use and to be removable from said device body;
   wherein said at least one drug-containing insert defines a right circular cylinder, extends substantially perpendicular to the main plane of the device body, and has a cross-sectional diameter of from about 0.5 mm to about 8 mm; and
   wherein the device body is a partial or complete toroid shape.

2. The intravaginal drug delivery device of claim 1, wherein said at least one drug is a macromolecular drug.

3. The intravaginal drug delivery device of claim 1, wherein said at least one drug is a water-soluble drug.

4. The intravaginal drug delivery device of claim 1, wherein said at least one drug is selected from proteins, RNA- or DNA-based molecules, vaccines, and combinations thereof.

5. The intravaginal drug delivery device of claim 4, wherein said proteins are selected from antibodies, antigens, adrenocorticotropic hormone, angiotensin, beta-endorphin, blood factors, bombesin, calcitonin, calcitonin gene relating polypeptide, cholecystokinin-8, colony stimulating factors, desmopressin, endothelin, enkephalin, erythropoietins, gastrins, glucagon, human atrial natriuretic polypeptide, interferons, insulin, growth factors, growth hormones, interleukins, luteinizing hormone release hormone, monoclonal antibodies, melanocyte stimulating hormone, muramyl-dipeptide, neurotensin, oxytocin, parathyroid hormone, peptide T, secretin, somatomedins, somatostatin, thyroid stimulating hormone, thyrotropin releasing hormone, thyrotropin stimulating hormone, vasoactive intestinal polypeptide, vasopressin, and their analogues or derivatives.

6. The intravaginal drug delivery device of claim 4, wherein said RNA- or DNA-based molecules are selected from oligonucleotides, aptamers, ribozymes, DNAzymes and small interfering RNAs, for either vaccination against sexually transmitted infections or microbicidal activity against sexually transmitted microorganisms.

7. The intravaginal drug delivery device of claim 4, wherein said vaccines are selected from whole viral particles, recombinant proteins, subunit proteins, DNA vaccines, plasmids, bacterial vaccines, polysaccharides and other vaccine vectors.

8. The intravaginal drug delivery device of claim 1, wherein said at least one drug is employed in an amount ranging from about 0.001% to about 50% by weight of the insert.

9. The intravaginal drug delivery device of claim 1, comprising first and second channels and first and second drug-containing inserts positioned in said first and second channels, respectively, wherein said first and second drug-containing inserts comprise drugs that may be the same or different.

10. The intravaginal drug delivery device of claim 1, comprising first, second and third channels, and first, second and third drug-containing inserts positioned, in use, in said first, second and third channels, respectively, wherein said first, second and third drug-containing inserts comprise drugs that may be the same or different.

11. The intravaginal drug delivery device of claim 1, wherein said hydrophobic carrier material is a polymeric material selected from a polydimethylsiloxane, a copolymer of dimethylsiloxane and methylvinylsiloxane, a polyurethane, and a poly(ethylene-co-vinyl acetate).

12. The intravaginal drug delivery device of claim 1, wherein said at least one water-soluble release enhancer is selected from the group consisting of sugars or their water-soluble salts; sugar alcohols; salts; glycols; water-soluble or water-swellable polysaccharides; organic acids; amino acids; proteins; nonionic surface active agents; bile salts; organic solvents; polyethylene glycols; fatty acid esters; hydrophilic polymers, and combinations thereof.

13. The intravaginal drug delivery device of claim 1, wherein said at least one drug-containing insert contains from about 15% to about 60% of said at least one water-soluble release enhancer by weight of said at least one drug-containing insert.

14. The intravaginal drug delivery device of claim 13, wherein said at least one drug-containing insert contains from about 15% to about 55% of said at least one water-soluble release enhancer by weight of said at least one drug-containing insert.

15. The intravaginal drug delivery device of claim 1, wherein the insert carrier material is a polymeric material selected from a polydimethylsiloxane, a copolymer of dimethylsiloxane and methylvinylsiloxane, a polyurethane, and a poly(ethylene-co-vinyl acetate).

16. The intravaginal drug delivery device of claim 1, wherein said hydrophobic carrier material, said insert carrier material, or both said hydrophobic and said insert carrier materials, comprise a silicone elastomer.

17. The intravaginal drug delivery device of claim 1, wherein said at least one drug-containing insert has a length of from about 2 mm to about 30 mm.

18. The intravaginal drug delivery device of claim 1, wherein the cross-sectional diameter of said at least one drug-containing insert exceeds the cross-sectional diameter of said channel by an average of about 1 mm in all directions.

19. The intravaginal drug delivery device of claim 1, wherein said at least one drug-containing insert further comprises at least one pharmaceutically acceptable non-water-soluble release enhancer in an amount ranging from about 1% to about 25% by weight of the insert.

20. The intravaginal drug delivery device of claim 1, wherein the device body further comprises at least one drug, particulate filler material, diffusion inhibitor, chemical penetration enhancer, water-soluble release enhancer or combination thereof.

21. The intravaginal drug delivery device of claim 20, wherein the at least one drug in the device body is selected from the group consisting of contraceptives, pain and migraine agents, drugs for hormone replacement therapy, anxiety and depression agents, drugs for the treatment of premenstrual syndrome, drugs for the treatment of genitourinary disorders, drugs for cervical ripening/induction of labor, antibacterials, antifungals, antimalarial agents, antiprotozoal agents, antiviral and antiretroviral agents, drugs for the treatment of endometriosis, anti-emetic drugs and osteoporosis drugs.

22. The intravaginal drug delivery device of claim 21, wherein the at least one drug is present in the device body in an amount ranging from about 0.005% to about 65% by weight of the device body.

23. The intravaginal drug delivery device of claim 20, wherein the water-soluble release enhancer in the device body is selected from the group consisting of sugars or their water-soluble salts; sugar alcohols; salts; glycols; water-soluble or water-swellable polysaccharides; organic acids; amino acids; proteins; nonionic surface active agents; bile salts; organic solvents; polyethylene glycols; fatty acid esters; and hydrophilic polymers, and combinations thereof.

24. The intravaginal drug delivery device of claim 20, wherein said device body contains less than about 10% of said water-soluble release enhancer by weight of said device body.

25. The intravaginal drug delivery device of claim 1, wherein the device body further comprises a sheath, provided that said at least one drug-containing insert is exposed on said exterior of said device body.

26. A method of preparing the intravaginal drug delivery device of claim 1 comprising the steps of:
  (a) molding said hydrophobic carrier material in the form of said device body defining at least one channel; and
  (b) inserting said at least one drug-containing insert into said at least one hollow internal channel such that said drug-containing insert is exposed on said exterior of said device body.

27. The method of claim 26 further comprising the step of curing the device body.

28. A method of intravaginally administering a drug to a female comprising the step of inserting the intravaginal drug delivery device of claim 1 into the vagina.

29. A method of preparing the intravaginal drug delivery device of claim 1 comprising the steps of:
  (a) molding said hydrophobic carrier material in the form of said device body defining at least one channel;
  (b) curing said insert material to form said at least one drug-containing insert; and
  (c) inserting said at least one drug-containing insert into said at least one hollow internal channel such that said drug-containing insert is exposed on said exterior of said device body.

* * * * *